(12) United States Patent
Karoly et al.

(10) Patent No.: US 11,298,085 B2
(45) Date of Patent: *Apr. 12, 2022

(54) METHODS AND SYSTEMS FOR FORECASTING SEIZURES

(71) Applicant: SEER MEDICAL PTY LTD, Fitzroy (AU)

(72) Inventors: Philippa Karoly, Fitzroy (AU); Dean Freestone, Fitzroy (AU); Mark Cook, Fitzroy (AU)

(73) Assignee: SEER MEDICAL PTY LTD

( * ) Notice: Subject to any disclaimer, the term of this patent is extended or adjusted under 35 U.S.C. 154(b) by 153 days.

This patent is subject to a terminal disclaimer.

(21) Appl. No.: 16/667,487

(22) Filed: Oct. 29, 2019

(65) Prior Publication Data

US 2020/0060627 A1 Feb. 27, 2020

Related U.S. Application Data

(63) Continuation of application No. 16/273,108, filed on Feb. 11, 2019, now Pat. No. 10,506,988, which is a
(Continued)

(30) Foreign Application Priority Data

Jul. 25, 2017 (AU) .............................. 2017-902920

(51) Int. Cl.
*A61B 5/00* (2006.01)
*A61B 5/0205* (2006.01)
(Continued)

(52) U.S. Cl.
CPC ............. *A61B 5/7275* (2013.01); *A61B 5/00* (2013.01); *A61B 5/0205* (2013.01); *A61B 5/24* (2021.01);
(Continued)

(58) Field of Classification Search
USPC ................................................... 600/300–301
See application file for complete search history.

(56) References Cited

U.S. PATENT DOCUMENTS

| 5,311,876 A | 5/1994 | Olsen et al. |
| 6,658,287 B1 | 12/2003 | Litt et al. |

(Continued)

FOREIGN PATENT DOCUMENTS

| WO | 2014138414 A1 | 9/2014 |
| WO | 2017007808 A1 | 1/2017 |

OTHER PUBLICATIONS

Schelter, B., et al., 'Seizure Prediction in Epilepsy: From Circadian Concepts via Probabilistic Forecasting to Statistical Evaluation'. 33rd Annual International Conference of the IEEE EMBS Boston, Massachusetts USA, Aug. 30-Sep. 3, 2011. pp. 1624-1672.
(Continued)

*Primary Examiner* — Nicole F Lavert

(57) ABSTRACT

A method of estimating the probability of a seizure in a subject, the method comprising: receiving historical data associated with epileptic events experienced by the subject over a first time period, the historical data comprising physiological data associated with each epileptic event and a time at which each epileptic event occurred; generating a temporal probability model of future epileptic events based on the time of each of the epileptic events, the temporal probability model representing a probability of a future seizure occurrence in each of a plurality of time windows; generating a probabilistic model based on the physiological data associated with each epileptic event; weighting the probabilistic model based on the temporal probability model to generate a weighted probabilistic model of future seizure activity; and outputting an estimate of seizure probability in the subject using the weighted probabilistic model.

21 Claims, 22 Drawing Sheets

Related U.S. Application Data continuation of application No. PCT/AU2018/050575, filed on Jun. 8, 2018.

(51) Int. Cl.

| | | |
|---|---|---|
| *A61B 5/24* | (2021.01) | |
| *A61B 5/316* | (2021.01) | |
| *A61B 5/374* | (2021.01) | |
| *A61B 5/375* | (2021.01) | |
| *G16H 50/30* | (2018.01) | |
| *A61B 5/021* | (2006.01) | |
| *A61B 5/024* | (2006.01) | |
| *A61B 5/11* | (2006.01) | |

(52) U.S. Cl.
CPC .............. *A61B 5/316* (2021.01); *A61B 5/374* (2021.01); *A61B 5/375* (2021.01); *A61B 5/4094* (2013.01); *A61B 5/4806* (2013.01); *A61B 5/7267* (2013.01); *A61B 5/742* (2013.01); *G16H 50/30* (2018.01); *A61B 5/021* (2013.01); *A61B 5/024* (2013.01); *A61B 5/1126* (2013.01); *A61B 5/4266* (2013.01); *A61B 2560/0252* (2013.01); *A61B 2560/0257* (2013.01); *A61B 2562/029* (2013.01); *A61B 2562/0219* (2013.01)

(56) References Cited

U.S. PATENT DOCUMENTS

| | | | |
|---|---|---|---|
| 2007/0213785 | A1 | 9/2007 | Osorio et al. |
| 2011/0270095 | A1 | 11/2011 | Bukhman |
| 2012/0310050 | A1* | 12/2012 | Osorio ............... A61B 5/02055 600/300 |

OTHER PUBLICATIONS

Karoly, P., et al., 'The circadian profile of epilepsy improves seizure forecasting'. BRAIN 2017. vol. 140. pp. 2169-2182. Jul. 26, 2017.
Alkan, A., et al. 'Automatic seizure detection in EEG using logistic regression and artificial neural network'. Journal of Neuroscience Methods vol. 148 (2005) pp. 167-176.
Subasi, A., et al., 'Classification of EEG signals using neural network and logistic regression'. Computer Methods and Programs in Biomedicine (2005) vol. 78. pp. 87-99.
Jachan, M., et al., 'Probabilistic Forecasts of Epileptic Seizures and Evaluation by the Brier Score' ECIFMBE 2008, FMBE Proceedings 22, pp. 1701-1705, 2008.
Loddenkemper, T., et al., 'Circadian patterns of pediatric seizures'. Neurology. Vol. 76. No. 2 pp. 145-153. 2011.
Kabir, E., et al., 'Epileptic seizure detection from EEG signals using logistic model Trees'. Brain Informatics (2016) vol. 3 pp. 93-100.
International Search Report and Written Opinion, as issued in connection with International Patent Application No. PCT/AU2018/050575, dated Jun. 8, 2018, 15 pgs.
U.S. Office Action in U.S. Appl. No. 16/273,108 dated May 2, 2019, 9 pages.
U.S. Notice of Allowance in U.S. Appl. No. 16/273,108, dated Aug. 8, 2019, 8 pgs.
Howbert et al., "Forecasting Seizures in Dogs with Naturally Occurring Epilepsy", PLOS ONE Issue 1 vol. 9 Jan. 2014.
"Effect of weather conditions on epileptic patients: a possible mechanism and its enlightenment for acupuncture therapy", RU Kai, Foreign medicine (Chinese traditional medicine part), vol. 19, No. 1, 1997, p. 61, Feb. 15, 1997.
"Study of the relationship between seizures and sleep cycles in children".
Chinese Office Action in CN Application No. 201880048689.1 dated Dec. 14, 2020, 10 pages.

* cited by examiner

| Subject | Design Seizures | Test Seizures | Test Duration (days) | Baseline Pre-ictal Rate |
|---|---|---|---|---|
| 1 | 18 (27) | 56 (93) | 534 | 0.73% |
| 2 | 4 | 23 (24) | 427 | 0.23% |
| 3 | 32 (87) | 129 (238) | 359 | 2.77% |
| 4 | 11 (12) | 2 | 23 | 0.36% |
| 5 | 2 (3) | 1 | 7 | 0.60% |
| 6 | 18 (25) | 21 (28) | 126 | 0.93% |
| 7 | 16 (116) | NA | 0 | NA |
| 8 | 45 (64) | 177 (245) | 360 | 2.84% |
| 9 | 44 (50) | 102 (115) | 193 | 2.50% |
| 10 | 70 (208) | 96 (267) | 174 | 6.43% |
| 11 | 26 (54) | 186 (289) | 448 | 2.68% |
| 12 | 1 | 5 | 447 | 0.05% |
| 13 | 63 (97) | 242 (373) | 469 | 3.32% |
| 14 | 0 | 10 (12) | 322 | 0.15% |
| 15 | 22 (24) | 36 (37) | 216 | 0.72% |

*Figure 2*

Total seizures during design and testing periods. Design phase seizures are the number of lead seizures between days 100 to 200 (total seizures in brackets, where different). Test seizures included lead seizures that occurred after the training period (number of days as shown). The baseline pre-ictal rate refers to the percentage of pre-ictal data during the test period (based on a 30-minute pre-ictal period before every seizure). Subjects shown in bold had at least 10 seizures in training and test periods, and were selected for the study

| Subject | Time in high risk (%) | Cook et. al. [2013] results | | New results (sensitivity) | | | |
|---|---|---|---|---|---|---|---|
| | | Test Seizures | Sensitivity | Test Seizures | Temporal (Circadian) | Logistic Regression | Temporal Logistic Regression (Circadian) |
| 1 | 27 | 13 | 0.77 | 56 | 0.34 | 0.54 | 0.61 |
| 3 | 29 | 106 | 0.45 | 129 | 0.36 | 0.53 | 0.55 |
| 6 | NA | NA | NA | 21 | 0.52 | 0.61 | 0.65 |
| 8 | 28 | 86 | 0.62 | 177 | 0.58 | 0.71 | 0.76 |
| 9 | 11 | 52 | 0.17 | 102 | 0.28 | 0.29 | 0.45 |
| 10 | 17 | 164 | 0.51 | 96 | 0.36 | 0.38 | 0.52 |
| 11 | 15 | 39 | 0.39 | 186 | 0.43 | 0.57 | 0.58 |
| 13 | 28 | 113 | 0.50 | 242 | 0.61 | 0.78 | 0.76 |
| 15 | 41 | 24 | 0.71 | 36 | 0.71 | 0.51 | 0.60 |

Figure 10: Prediction performance and results. The number of test seizures (lead seizures, defined as having a preceding seizure-free interval of at least five hours, and trial results during the four-month assessment phase of the original clinical trial. The new results for the three forecasting models are reported (based on a matched proportion of time in warning, see Supplementary material for exact time in warning data). Sensitivity was calculated according to Cook et al. (2013). The highest sensitivity is underlined for each subject.

*Figure 10*

| Patient | Temporal Logistic Regression (Circadian) | Temporal (Circadian) | Logistic regression | Cook et al. [2013] |
|---|---|---|---|---|
| 1 | 0 | 0 | 0 | 7 |
| 6 | 24 | 0 | 0 | NA |
| 8 | 11 | 19 | 0 | NA |
| 9 | 30 | 31 | 19 | 48 |
| 10* | 17 | 11 | 10 | NA |
| 11 | 34 | 30 | 0 | 26 |
| 15 | 38 | 30 | 30 | NA |

Figure 11: Time in low risk (%) for each forecasting model. Low risk activation was modeled using the triggering scheme described in Cook et al. (2013). Zero indicates a threshold could not be found based on the design phase data (day 100 – day 200). NA indicates that the low risk advisory state was not enabled in the NeuroVista trial. Note that no threshold could be found for Subjects 3 and 13 in either the current or previous study. *Subject 10 had one seizure during their low-risk advisory test period (after day 200). All other subjects had no seizures during their low-risk advisory test period.

*Figure 11*

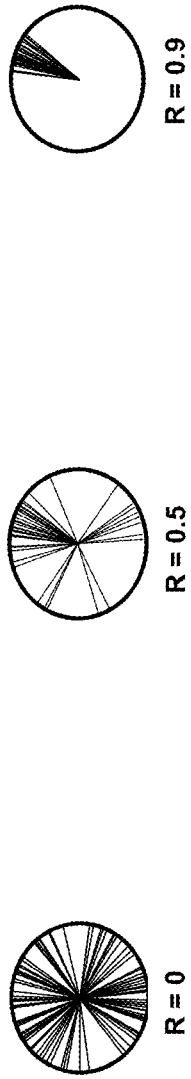
Figure 13A  Figure 13B  Figure 13C
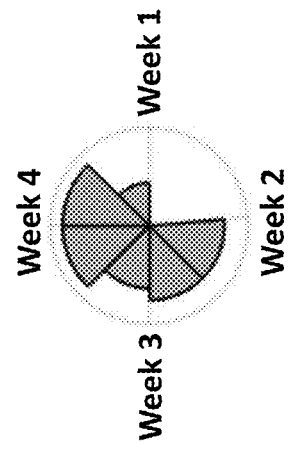
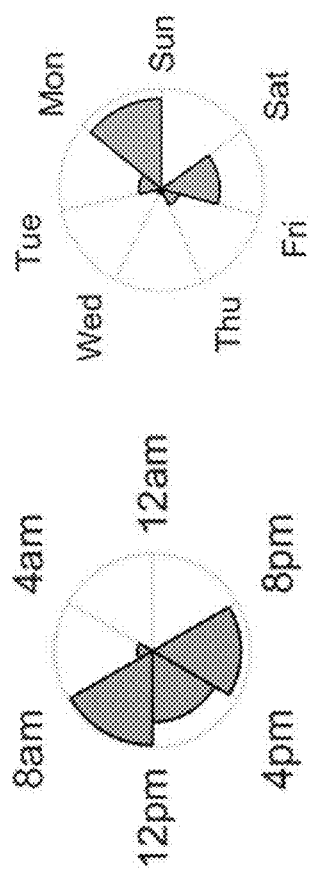
Figure 14A  Figure 14B  Figure 14C

METHODS AND SYSTEMS FOR FORECASTING SEIZURES

TECHNICAL FIELD

The present disclosure relates to methods and systems for or forecasting seizure likelihood in epilepsy patients using probabilistic modelling.

BACKGROUND

The unpredictability of seizures has a profound impact on their safety of people with epilepsy. Accurate seizure forecasting would greatly improve an individuals' quality of life, potentially enabling pre-emptive administration of therapies or allowing steps to ensure personal safety to be undertaken.

It is well established that seizures in many patients are preceded by a measurable change in brain state. Attempts have been made in the past to implement methods for forecasting whether a seizure is going to occur based on these brain state changes. To date, such techniques for forecasting seizures suffer from poor generalizability due to the relatively short duration of available historical data.

The first human trial for an implantable warning system was reported in Cook et al, 2013 (*Prediction of seizure likelihood with a long-term, implanted seizure advisory system in patients with drug-resistant epilepsy: a first-in-man study*. The Lancet Neurology 2013; 12(6): 563-71), the contents of which is hereby incorporated by reference in its entirety. This study demonstrated the viability of seizure forecasting from intracranial electrical recordings (electroencephalography) for patients with intractable epilepsy. The resultant increase in available long-term data has inspired a renewed focus on implementing predictive methods that are both patient- and seizure-specific.

Despite recent forecasting advances, traditional assessment metrics for seizure prediction continue to be based on categorical statements—a seizure either will or will not happen—and are inappropriate for assessing probabilistic forecasts.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to an aspect of the disclosure, there is provided a method of estimating the probability of a seizure in a subject, the method comprising: receiving historical data associated with epileptic events experienced by the subject over a first time period, the historical data comprising physiological data associated with each epileptic event and a time at which each epileptic event occurred; generating a temporal probability model of future epileptic events based on the time of each of the epileptic events, the temporal probability model representing a probability of a future seizure occurrence in each of a plurality of time windows; generating a probabilistic model based on the physiological data associated with each epileptic event; weighting the probabilistic model based on the temporal probability model to generate a weighted probabilistic model of future seizure activity; and outputting an estimate of seizure probability in the subject using the weighted probabilistic model.

The temporal probability model may be a circadian probability model, i.e. a model of the probability of future epileptic events based on the time of each epileptic event over a 24 hour time period. Alternatively, the temporal probability model may be ultradian or infradian, i.e. a model of the probability of future epileptic event over a time period which is less than (ultradian) or greater than (infradian) 24 hours. In any case, the temporal probability model may enable forecasting of seizures in the subject over any time period (ultradian, infradian or circadian).

The physiological data may comprise an electroencephalography (EEG) signal received from a brain of the subject. The EEG signal may be an intracranial EEG signal or an EEG signal measured external to the skull. The method may further comprise filtering the EEG data. The EEG data may be filtered using analogue or digital filtering techniques or a combination thereof. The EEG data may be filtered using a bandpass filter. The physiological data may comprise determinations of sleep quality for the patient. Such determinations may be derived from the EEG signal.

The probabilistic model may be a logistic regression model. In which case, generating the logistic regression model may comprise: determining, for a logistic regression classifier, a set of features in the physiological data; and training the logistic regression model using the set of features.

The set of features may comprise a line length feature and/or one or more energy features. Each of the one or more energy features may be at a different frequency band. Frequency bands may include 8-16 Hz, 16-32 Hz, 32-64 Hz, and 64-128 Hz. The method may further comprise applying a moving average filter to the set of features.

In some embodiments, the line length L is given by $L=\Sigma_{k=t-1999}^{t}|x(k-1)-x(k)|$, where $x(t)$ is the EEG signal at time, t.

The logistic regression model may be trained to output the probability, $P(S=1|X)$, that a feature vector, X, is pre-ictal.

The logistic regression model may be given by $$P(S=1|X) = \frac{1}{1+\exp\left(w_0 + \sum_{i=1}^{N} w_i X_i\right)},$$

where N is the number of features in the set of features and $w_0$ is a bias operable to shift an intercept of the logistic regression model.

Weighting the probabilistic model may comprise updating the weights of the logistic regression classifier based on the temporal probability model.

Generating the temporal probability model may comprise estimating a probability density function based on the times at which each epileptic event occurred.

The probability density function may be estimated using kernel density estimation. In which case, the estimated probability density may be given by $$\hat{p}(x) = \frac{1}{K\sum_{i=1}^{N} f(x|\mu_i, \kappa)},$$

where N is the number of kernels, $\mu_i$ is the center of the $i^{th}$ kernel, and $\kappa$ is a tuning factor for tuning the width of the estimation kernel. K is a normalizing constant and may be given by $$\int_0^{24} \sum_{i=1}^{N} f(x \mid \mu_i, \kappa) dx$$

The temporal probability model may be generated by combining two or more probability density functions each function derived from data associated with epileptic events in the patient, such as times at which epileptic events occur.

The two or more probability density functions may be combined by repeated application of Bayes theorem. Bayes theorem may be stated mathematically as the following equation.

$$P(S \mid X) = \frac{P(X \mid S) P(S)}{P(X)}$$

where X is the observation (time, temperature, etc) and S is the occurrence of a seizure in some future time window.

If the probabilistic model is given by the logistic regression classifier, then time-weighted probabilistic model may be given by $$P(S = 1 \mid X) = \frac{1}{1 + \exp\left( \log \frac{1 - P_S}{P_S} + \log \frac{P(X \mid S = 0)}{P(X \mid S = 1)} \right)}$$

where $P_S$ represents the prior probability of a seizure occurring in one of the set of time windows.

In some embodiments, the probabilistic model may generate a probabilistic output between 0 and 1, where 0 is an estimated 0% likelihood that a seizure will occur and 1 is an estimated 100% likelihood that a seizure will occur. In which case, probabilistic model may be weighted by combining the temporal probability model with the probabilistic model using Bayes theorem.

The physiological data may comprise one or more of:
heart rate data;
blood pressure data;
sweat data;
movement data measured by an accelerometer worn by the patient
sleep quality data, which may be derived from an EEG as discussed above or reported by the subject.

The time at which each epileptic event occurred may be measured from the time of a previous epileptic event. Alternatively, the time at which each epileptic event occurred may be measured using a 24-hour clock, i.e. over a circadian rhythm. Alternatively, the time at which each epileptic event occurred may be measured over some other ultradian or infradian time period. The time period over which each epileptic event occurrence is measured may be adjusted based on a history of epileptic events associated with the patient being monitored. For example, the rhythm of increased probability of an epileptic event may follow an ultradian cycle or infradian cycle and that ultradian or infradian cycle may be used as a time frame over which to measure the time at which each epileptic event occurred.

The epileptic events may be associated with seizures of the subject. Equally, the epileptic evens may be associated with abnormalities in the physiological data.

In some embodiments, the historical data further comprises values of one or more environmental variables associated with each epileptic event. In such embodiments, the method may further comprise generating an environmental probability model of future epileptic events based on the environmental variables associated with each epileptic event, the environmental probability model representing a probability of a future seizure occurrence over a range of values of the one or more environmental variable; and weighting the probabilistic model based on the environmental probability model to generate the weighted probabilistic model of future seizure activity.

The one or more environmental variables may comprise one or more of temperature, humidity, wind speed, barometric pressure, rainfall.

The historical data may further comprise values of one or more variables of sleep associated with each epileptic event. In which case, the method may further comprise: generating a sleep probability model of future epileptic events based on the sleep variables associated with each epileptic event, the sleep probability model representing a probability of a future seizure occurrence over a range of values of the one or more sleep variable; and weighting the probabilistic model based on the sleep probability model to generate the weighted probabilistic model of future seizure activity.

The one or more sleep variables may comprise one or more of hours awake over a 24 hour period, hours asleep over a 24 hour period, and sleep depth.

According to another aspect of the disclosure, there is provided a seizure advisory system, comprising: an input for receiving historical data associated with epileptic events experienced by the subject over a first time period, the historical data comprising physiological data associated with each epileptic event and a time at which each epileptic event occurred; a processor configured to: generate a temporal probability model of future epileptic events based on the time of each of the epileptic event, the temporal probability model representing a probability of a future seizure occurrence over a set of time windows; generate a probabilistic model based on the physiological data associated with each epileptic event; weight the probabilistic model based on the temporal probability model to generate a weighted probabilistic model of future seizure activity; and output an estimate of seizure probability in the subject using the weighted probabilistic model.

The system may further comprise memory to store the estimate of seizure probability and other data, such as some or all of the historical data.

The system may further comprise one or more measurement devices configured to record the physiological data. The one or more measurement devices may comprise one or more of the following:
an EEG sensor;
a heart rate monitor;
a blood pressure monitor
a sweat sensor;
an accelerometer;
a gyroscope.

Each measurement device may be configured for recording of the physiological data.

The EEG sensor may comprise a lead having at least one electrode for recording neural activity at a neural structure in a brain of the subject. The physiological data may comprise the recorded neural activity. The lead may be implanted intracranially in the brain of the subject.

The physiological data may comprise an electroencephalography (EEG) signal received from the brain of the subject.

The system may further comprise one or more filters for filtering the physiological data. The filters may be analogue or digital or a combination thereof. The one or more filters may include one or more bandpass filters.

The probabilistic model may be a logistic regression model. In which case, generating the logistic regression model may comprise: determining, for a logistic regression classifier, a set of features in the physiological data, the set of features; training the logistic regression model using the set of features.

The set of features may comprise a line length feature and/or one or more energy features each at a different frequency band. Frequency bands may include 8-16 Hz, 16-32 Hz, 32-64 Hz, and 64-128 Hz. The method may further comprise applying a moving average filter to the set of features.

In some embodiments, the line length is given by $L=\Sigma_{k=t-1999}^{t}|x(k-1)-x(k)|$, where x(t) is the EEG signal at time, t.

The logistic regression model may be trained to output the probability, $P(S=1|X)$, that a feature vector, X, is pre-ictal.

The logistic regression model may be given by $$P(S=1 \mid X) = \frac{1}{1+\exp\left(w_0 + \sum_{i=1}^{N} w_i X_i\right)},$$

where N is the number of features in the set of features and $w_0$ is a bias operable to shift an intercept of the logistic regression model.

Weighting the probabilistic model may comprise updating the weights of the logistic regression classifier based on the temporal probability model.

Generating the temporal probability model may comprise estimating a probability density function based on the times at which each epileptic event occurred.

The probability density function may be estimated using kernel density estimation. In which case, the estimated probability density may be given by $$\hat{p}(x) = \frac{1}{K \sum_{i=1}^{N} f(x \mid \mu_i, \kappa)},$$

where N is the number of kernels, $\mu_i$ is the center of the $i^{th}$ kernel, $\kappa$ is a tuning factor for tuning the width of the estimation kernel. K is a normalizing constant and may be given by $$\int_{0}^{24} \sum_{i=1}^{N} f(x \mid \mu_i, \kappa) dx$$

The time-weighted probabilistic model may be given by $$P(S=1 \mid X) = \frac{1}{1+\exp\left(\log\frac{1-P_S}{P_S} + \log\frac{P(X \mid S=0)}{P(X \mid S=1)}\right)}$$

where $P_S$ represents the prior probability of a seizure occurring in one of the set of time windows.

where $P_S$ represents the prior probability of a seizure occurring in one of the set of time windows.

The system may further comprise a display. The estimate of seizure probability may be output to the display, optionally alongside other data.

In some embodiments, the historical data further comprises values of one or more environmental variables associated with each epileptic event and the processor is further configured to: generate an environmental probability model of future epileptic events based on the environmental data associated with each epileptic event, the environmental probability model representing a probability of a future seizure occurrence over a range of values of the one or more environmental variable; and weight the probabilistic model based on the environmental probability model to generate the weighted probabilistic model of future seizure activity.

The one or more environmental variables may comprises one or more of temperature, humidity, wind speed, barometric pressure, rainfall.

In some embodiments, the historical data further comprises values of one or more variables of sleep associated with each epileptic event, and the processor is further configured to: generate an sleep probability model of future epileptic events based on the sleep variables associated with each epileptic event, the sleep probability model representing a probability of a future seizure occurrence over a range of values of the one or more sleep variable; and weight the probabilistic model based on the sleep probability model to generate the weighted probabilistic model of future seizure activity.

The one or more sleep variables may comprises one or more of hours awake over a 24 hour period, hours asleep over a 24 hour period, and sleep depth.

According to another aspect of the disclosure, there is provided a method of estimating the probability of a seizure in a subject, the method comprising: receiving historical data associated with epileptic events experienced by the subject over a first time period, the historical data comprising physiological data associated with each epileptic event and an environmental variable associated with each epileptic event; generating an environmental probability model of future epileptic events based on the environmental variable associated with each epileptic event, the environmental probability model representing a probability of a future seizure occurrence over a range of values of the environmental variable; generating a probabilistic model based on the physiological data associated with each epileptic event; weighting the probabilistic model based on the environmental probability model to generate a environment-weighted probabilistic model of future seizure activity; and outputting an estimate of seizure probability in the subject using the environment-weighted probabilistic model.

The environmental variable may comprises one or more of temperature, humidity, wind speed, barometric pressure, rainfall.

According to another aspect of the disclosure, there is provided a seizure advisory system comprising: an input for receiving historical data associated with epileptic events experienced by the subject over a first time period, the historical data comprising physiological data associated with each epileptic event and an environmental variable associated with each epileptic event; a processor configured to: generate an environmental probability model of future epileptic events based on the environmental variable associated with each epileptic event, the environmental probability model representing a probability of a future seizure occurrence over a range of values of the environmental variable; generate a probabilistic model based on the physiological data associated with each epileptic event; weight the probabilistic model based on the environmental probability model to generate a environment-weighted probabilistic model of future seizure activity; and output an estimate of seizure probability in the subject using the environment-weighted probabilistic model.

The environmental variable may comprises one or more of temperature, humidity, wind speed, barometric pressure, rainfall.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

FIG. 2 is a table showing the number of seizures and baseline pre-ictal rates for fifteen patients undergoing long-term electrocorticography (ECoG) monitoring;

FIG. 10 is a table showing prediction performance and results with a sensitivity for a temporal logistic regression model, a logistic regression model, and temporal model;

FIG. 11 is a table showing the time spent in low-risk advisory phase for each of a temporal logistic regression model, a logistic regression model, and temporal model;

FIGS. 13A, 13B and 13C are histograms of seizures representing a mean resultant length of R=0, R=0.5 and R=0.9 respectively for an arbitrary cycle phase and duration;

FIGS. 14A, 14B and 14C are histograms shown seizure occurrence for three different subjects over three different temporal cycles;

DESCRIPTION OF EMBODIMENTS

Figure 1:
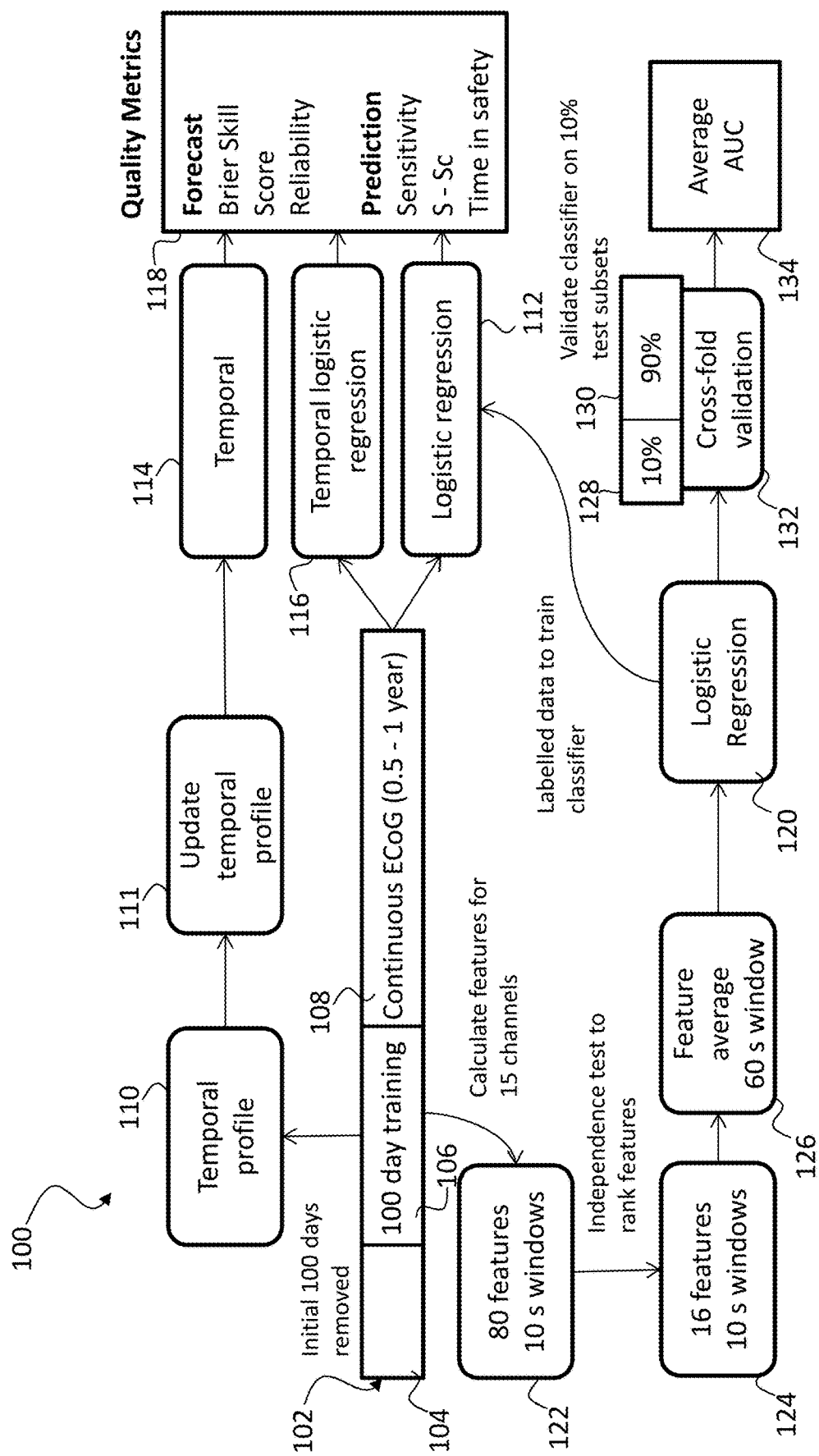
FIG. 1 is a schematic diagram illustrating methods for generating and evaluating a temporal logistic regression model according to an embodiment of the disclosure.

Embodiments of the present disclosure provide a probabilistic approach to seizure prediction that incorporates prior knowledge about underlying patterns in seizure occurrence with respect to other variables that affect the probability of a subject or patient having a seizure. In particular, there is overwhelming evidence that epilepsy adheres to cyclic patterns that modulate seizures and seizure susceptibility at certain times of day. The periods of highest seizure likelihood vary greatly between patients, but on an individual level remain consistent over many years. Tracking and utilizing temporal patterns of seizures presents an exciting opportunity to enhance patient management. This patient-specific timing information can be used to titrate treatment and improve the performance of seizure advisory systems.

In addition to the harnessing of patient specific temporal profiles for improving seizure forecasting and advisory systems, the inventors have realised that weather conditions also impact seizure susceptibility on a patient specific level. Embodiments of the present disclosure aim to improve the accuracy of seizure forecasting by taking into account historical and current environmental conditions (e.g. temperature).

Brier Score

A forecasting approach that expresses the current degree of belief as a likelihood or probability (and incorporates prior information) is grounded in a probabilistic Bayesian epistemology. Traditional assessment metrics for seizure prediction are based on categorical statements—a seizure either will or will not happen—and are inappropriate for assessing probabilistic forecasts. However, in reality, the brain can enter a state of high seizure likelihood that does not necessarily terminate in a clinical seizure, challenging the traditional definition of a false positive prediction. The challenge of assessing probabilistic forecasts was addressed in the meteorological community by Brier (1950), who introduced the Brier score to measure the probability error of weather forecasts. Since Brier's seminal work, meteorologists have spent decades refining attributes of forecasting 'goodness', and developing metrics to measure these different attributes.

Assessment of seizure prediction can benefit by applying additional probabilistic metrics using techniques from weather forecasting. Several approaches exist for the assessment of seizure prediction performance compared to chance outcomes. However, these methods are based on a categorical, rather than probabilistic prediction.

Henceforth, the terms 'forecast' and 'prediction' will be used to differentiate between probabilistic and categorical statements about whether a seizure will occur within some future window. Ultimately, the final categorical prediction is the most clinically relevant outcome. However, it may also be possible, and even preferable, to improve prediction algorithms by first optimizing aspects of forecasting performance.

The Brier score measures the difference between a continuous, probabilistic forecast and the observed rate of seizures, without requiring an explicit prediction to be made. The Brier score assesses an arbitrarily long sequence of consecutive forecasts over a continuous recording period, providing an excellent framework to assess and compare predictive models without additional tuneable parameters, such as true and false positive rates. Minimizing the number of tenable parameters reduces the risk of in-sample optimization, thus increasing confidence that observed results will generalize to future data.

The Brier score has previously been used to evaluate seizure forecasting. However, it is difficult to implement for rare event forecasting unless large amounts of observation data are available. Previous seizure prediction results have been based on short-term (typically one week) recordings from patients undergoing pre-surgical monitoring, and this limited time-span is insufficient to build patient-specific models of seizure likelihood. Furthermore, there are acute and sub-acute effects of device implantation and hospitalization which mean that short-term data may not provide a reliable test-case scenario for building implantable prediction algorithms.

As will be discussed in more detail below, embodiments of the present disclosure utilise long-term data from a previous study measured over a total period of 900 days for algorithm training, and 2879 days for testing, to evaluate novel patient-specific forecasting models which have been developed by the inventors. This recording duration provides an excellent opportunity to evaluate these novel methods of probabilistic seizure forecasting. The large amount of testing data provides confidence that the predictive models discussed are not simply optimized for a small number of seizures. On the contrary, the resulting analyses present a proof-of-concept for updating seizure forecasts based on each and all of patient-specific temporal information, patient-specific environmental information, and patient-specific sleep information.

Methodology

Data used to develop some of the methods described herein was collected from a clinical trial of an implantable seizure warning device, reported in Cook et al, 2013 (*Prediction of seizure likelihood with a long-term, implanted seizure advisory system in patients with drug-resistant epilepsy: a first-in-man study*. The Lancet Neurology 2013; 12(6): 563-71), the contents of which is hereby incorporated by reference in its entirety. This data was accessed from the International Epilepsy Electrophysiology Portal (ieeg.org).

All subjects of this trial had focal onset seizures, with a seizure onset zone identified from pre-existing medical records and neuroimaging. Intracranial electrode arrays with a total of 16 platinum iridium contacts were implanted around the seizure onset zone. The electrocorticography (ECoG) was sampled at 400 Hz and wirelessly relayed to an external, portable, personal advisory device. Seizure detection was automated using a proprietary detection method. All detections were verified by expert investigators with the aid of audio recording from the handheld device and subjects' seizure diaries.

Seizures were classified as being either clinical (type 1) or clinically equivalent (type 2). Type 1 events were associated with clinical symptoms; type 2 events had no verified clinical symptoms but were electroencephalographically indistinguishable from clinical seizures. Based on the similarity of the ECoG, type 2 seizures were considered relevant for developing methods of seizure prediction, and types 1 and 2 seizures are treated equivalently in this work. Additionally, subclinical (type 3) seizures were detected in the Cook et al. (2013) study, but these were excluded for the development of the algorithmic methods described in embodiments of the present disclosure. Type 3 events were not clinically manifest and had an electroencephalographic signature that differed from type 1 and 2 events. Prior to analysis, the ECoG was filtered between 1 Hz-140 Hz using a zero-phase second-order Butterworth bandpass filter.

FIG. 1 is a schematic diagram 100 outlining methods of generating and evaluating forecasting models according to embodiments of the disclosure. Methods were implemented using historical data 102 taken from clinical trials discussed above (Cook et al, 2013.).

For each subject, the first hundred days 104 of data recorded in those trials were discounted from analysis due to disruption of the signal resulting from device implantation. The second hundred days of data (training phase data 106) were used for the algorithm design phase to generate a temporal profile 110 of epileptic events as well train a logistic regression classifier 112. The remaining data from day 200 onwards (evaluation data 108), which ranged from six months to over a year of continuous recording for each subject, was used to update (step 114) the temporal profile 110 generated using the training phase data 106. The evaluation data 108 was also used to evaluate the prospective forecasting performance of each of three models 112, 114, 116. The updated temporal profile 111 was used to generate a temporal probability model 114. The temporal probability model 114 and the logistic regression model 112 were then combined to generate a temporal logistic regression model 116.

Each of the three models—combined temporal logistic regression 116, logistic regression only 112, and temporal probability only 114—were evaluated using quality metrics 118. Forecasting models output the probability that a seizure would occur within the next 30 minutes (the pre-ictal period), and made a forecast every 30 seconds (a 60 second sliding window with 50% overlap).

The Probabilistic models 112, 114, 116 were generated using lead seizures only (i.e. seizures preceded by at least a 5-hour seizure-free interval). Subjects with 10 or more lead seizures during the 100-day training phase 106 were selected for the study, resulting in a total of nine subjects. These subjects had an average of 38 lead seizures in the 100-day training phase 106, and an average of 116 lead seizures during the remaining evaluation period 108. A breakdown of the total number of seizures experienced by subjects are provided in FIG. 2. Referring to this Figure, "Design Seizures" are lead seizures which took place in the training phase 106 (total number in brackets), and "Test Seizures" are lead seizures which took place during the evaluation period 108 (total number of seizures in brackets). The "Test Duration" column provides the duration of the evaluation period 108 for each subject. The baseline pre-ictal rate column refers to the percentage of pre-ictal data during the test period (based on a 30-minute pre-ictal period before every seizure).

Logistic Regression Model

Referring again to FIG. 1, logistic regression classifiers 120 were trained on select segments of data taken from the 100-day algorithm training phase 106. Data were chosen from inter-ictal and pre-ictal periods. Pre-ictal periods were defined as being a 30-minute window ranging from 31 minutes to 1 minute prior to a lead seizure. Inter-ictal segments were chosen to be 30-minute periods at least six hours clear of a seizure (before or after). The number of inter-ictal segments was matched to the number of pre-ictal segments, giving a balanced training dataset. Balanced training data can lead to the model being biased towards over-identifying pre-ictal segments. Such bias can be adjusted by shifting the logistic regression intercept.

ECoG data, which was pre-processed by filtering (e.g. bandpass filtering between 1 Hz-140 Hz using a 2nd order zero-phase Butterworth filter), was then converted to a vector of possible features for each channel. Features were calculated for a 10 s sliding window, advanced in 5 s increments (FIG. 1, 122). Features were similar to those used in the original NeuroVista clinical trial described in (Cook et al., 2013), the contents of which is herein incorporated by reference in its entirety. In particular, five features were used: line length and the energy in four different frequency bands (8-16 Hz, 16-32 Hz, 32-64 Hz, and 64-128 Hz). Line length is given by $$L = \sum_{k=t-1999}^{t} |x(k-1) - x(k)|,$$

where x(t) is the ECoG signal at time, t. Features were calculated for each of the 16 electrode channels, resulting in a total of 80 possible features (16×5=80). From 80 possible features, a final set of 16 were selected (FIG. 1, 124) by taking the features with the highest relative entropy (Kullback-Leibler distance) over the training subset (using the MATLAB® function rankfeatures). The features were then smoothed by taking an average over a 60 s-moving window (FIG. 1, 126).

For each subject the entire set of smoothed and labelled feature vectors 120 were assigned into chronologically ordered training (90% of the data) and test (10% of the data) subsets 128, 130. Division was repeated 10 times (subsets chosen sequentially without replacement) to assess average performance (10-fold cross-validation) (FIG. 1, 132). The training feature vectors were then used to fit the weights of the logistic regression function.

The logistic regression model, which was trained to output the probability that a feature vector, X, is pre-ictal (S=1), is given by $$P(S = 1 | X) = \frac{1}{1 + \exp\left(w_0 + \sum_{i=1}^{N} w_i X_i\right)},$$ (1)

where N=16 and $w_0$ is a bias (intercept). The weights, $w=[w_0, \ldots, w_N]$ were learned from training data using the method of iterative re-weighted least squares with L1 regularization described in Lee et al, "*Efficient L1 regularized logistic regression*". *Proceedings of the National Conference on Artificial Intelligence;* 2006; 2006. p. 401, the contents of which is hereby incorporated by reference in its entirety.

To validate the performance of the logistic regression classifier, the area under the curve (AUC) 134 was calculated for the test subset 128 for each stage of cross-fold validation. In all instances, validation gave above-chance performance. As such, the final logistic regression classifier was trained using all the pre-ictal and inter-ictal feature vectors obtained from the 100-day training period. The final logistic regression classifier was evaluated in a prospective manner using the remaining data (after day 200).

Temporal Probability Model

The temporal profile 110 was created for each subject based on their seizure times (in 24-hour UTC time) during the 100-day algorithm training phase 106. A probability density function was estimated from the histogram of seizure times using kernel density estimation. Initially, the temporal profile 110 was created by determining a circadian rhythm, i.e. the distribution of seizure times over the 24 hour time period of a day. Since time of day is a periodic variable the circular normal (von-Mises) distribution was used as an estimation kernel. The von-Mises distribution is given by $$f(x | \mu, \kappa) = \frac{\exp(\kappa \cos(x - \mu))}{2\pi I_0 \kappa},$$ (2)

Where $I_0$ is a zero-order modified Bessel function. The parameters µ and $$\frac{1}{\kappa}$$

are analogous to the mean and variance of the normal distribution. The estimated probability density is given by $$\hat{p}(x) = \frac{1}{K \sum_{i=1}^{N} f(x | \mu_i, \kappa)},$$ (3)

where N is the number of kernels, $\mu_i$ is the centre of the $i^{th}$ kernel and κ tunes the width of the estimation kernel (width is proportional to $$\frac{1}{\kappa}\bigg).$$

K is a normalizing constant given by $$\int_0^{24} \sum_{i=1}^{N} f(x | \mu_i, \kappa) dx,$$ (4)

which ensures the area under $\hat{p}(x)$ is equal to 1. K may be estimated numerically, for example, using the trapz function in MATLAB®.

Whilst in the embodiments described above, kernel density estimation is used to refine the probability density function, in other embodiments, this step may be skipped and the probability density function generated without kernel density estimation.

To estimate the probability of a seizure occurring in any particular hour (assuming a bin width of one hour), 24 kernels were used with mean, µ=0, . . . , 23 and set $$\frac{1}{\kappa} = 0.6.$$

A uniform prior can be assumed. Then, the calculation of $\hat{p}(x)$ can be iterated by re-weighting the sum, such that the contribution of each kernel to $\hat{p}(x)$ is proportional to the number of seizures within that hour, $$\hat{p}(x) = \frac{1}{K \sum_{i=1}^{N} W_i f(x|\mu, \kappa)}, \quad (5)$$

where for $n_i$ seizures in the $i^{th}$ hour, $$W_i = \frac{n_i}{N}$$

(note the assumption of a uniform prior is equivalent to assuming that initially $n_i=1$ for all i). This iterative calculation enables the probability density function to be updated 110 after every seizure, providing a progressive estimation of the temporal profile 114. As mentioned above, initially the probability functions were created from histograms with a bin width of one hour (i.e. 24 kernels for a circadian cycle), which governed the time sensitivity of the model. It will be appreciated that in other embodiments, the bin width could be selected to be a different duration, e.g. 30 minutes to increase the time sensitivity of the model or 2 hours to decrease the time sensitivity.

In addition or as an alternative to estimating a probability density function for seizure times over a circadian (24 hour) cycle, one or more additional probability functions may be estimated over different time periods either longer (infradian) or shorter (ultradian) than the circadian time period. For example, time periods over which seizure probability can be modelled may include weeks, months, years, or the like. The above techniques used to estimate a probability density function and seizure probability for a circadian cycle may be used to generate similar functions and probability for any other time period.

As mentioned above, the bin width may be selected to be any suitable duration. For example, a bin width of one day may be used for a one week (7 day) or one month cycle.

Circadian Logistic Regression

The logistic regression 112 and temporal 114 models were combined by iteratively updating the weights of the logistic regression classifier 120. The weight update was based on the subject-specific estimate of the probability of seizure occurrence given the time of day (given by equation 5 above). The temporal logistic regression model may be expressed as follows $$P(S=1|X) = \frac{P(X|S=1)P(S=1)}{P(X|S=1)P(S=1) + P(X|S=0)P(S=0)} \quad (6)$$

$$= \frac{1}{1 + \exp\left(\log\frac{1-P_S}{P_S} + \log\frac{P(X|S=0)}{P(X|S=1)}\right)}$$

Where $P_S$ represents the prior probability of a seizure occurring in that hour (given by Equation 5).

To update the prior probability of the logistic regression model, it can be seen from Equation 6 that $w_0$ may be recalculated as $w_0'$, where $$w_0' = w_0 - \log\left(\frac{P_S}{1-P_S} \frac{1-P_S'}{P_S'}\right). \quad (7)$$

Where $P_S$ is the prior inferred from the training data (proportion of training data that was labelled as pre-ictal) and $P_S'$ is the prior to be used. This update may be applied every hour (or other time period) to reflect the probability of seizure based on time of day.

Performance Assessment

A range of metrics was used for performance assessment, each of which addressed distinct questions. During algorithm validation, performance was assessed using the receiver-operating characteristic (area under the curve, AUC). The AUC addresses the ability of a logistic regression classifier to discriminate between inter-ictal and pre-ictal data. Additional measures were used to evaluate the prospective performance.

The following metrics were used to measure probabilistic forecast quality:

Reliability curve: How well do the predicted probabilities of an event correspond to their observed frequencies?

Brier score: What is the magnitude of the probability forecast errors?

Brier skill score: What is the relative skill, or performance, of different probabilistic forecasts?

Investigating more traditional notions of prediction quality required an additional prediction rule for each forecasting model. A high and low probability threshold was used to trigger high and low risk warnings, as outlined by Snyder D E, et al., "*The statistics of a practical seizure warning system.*", Journal of neural engineering 2008; 5(4): 392, the contents of which is hereby incorporated by reference in its entirety. The warning triggered by a threshold crossing was switched on for $\tau_w$, which was set between 30 to 60 minutes duration. For a warning to be considered a true positive, the high risk seizure indicator was required to be on for at least 5 minutes before seizure ($\tau_{w_0}$). The same requirement was applied for the low risk seizure indicator to be considered a true negative.

The following metrics were then applied:

Time in safety: What is the maximum amount of time a patient could be assured of low-risk status without a seizure occurring?

Prediction sensitivity: How many seizures were correctly identified to occur during high-risk periods?

Sensitivity improvement-over-chance: How valuable was the high-risk warning light, considering the length of time spent in warning?

Brier Score

To calculate the Brier score, the forecast of seizure likelihood is first quantized into probability bins (typically 0-10% and so on until 90%-100%). The quantization step size reflects meaningful increments for a device and is limited by the number of seizures that occur. After quantization, the forecast is compared to observation data, which is coded into either 0 or 1 (a seizure does or does not occur in the next 30 minute pre-ictal period). The quantization approach enables reliability curves to be constructed, as discussed in the following section. A perfect Brier score is 0 (a forecast of 100% for every seizure), and the worst possible score is 1. Essentially the Brier score measures the mean squared error over every forecast; however, a more useful decomposition is given by:

BS=Reliability−Resolution+Uncertainty.

Uncertainty accounts for the baseline rate of seizures. The Resolution quantifies the average predictive power above the baseline rate. Reliability describes how close the forecast probability is to the observed data, i.e. the true rate of seizures, given a certain forecast is made. Each term is computed by:

$$\text{Reliability} = \frac{1}{N}\sum_{i=1}^{N_f} n_i(f_i - b_i)^2,$$

$$\text{Resolution} = \frac{1}{N}\sum_{i=1}^{N_f} (b_i - b)^2,$$

$$\text{Uncertainty} = b(1 - b).$$

Where N is the total number of forecasts (number of 60 s windows), $N_f$ is the number of forecast bins (10 was used), b is the baseline pre-ictal rate of seizures (see FIG. 2), $b_i$ is the actual seizure occurrence rate when the forecast was in the $i^{th}$ bin, and $f_i$ is the average forecast for the $i^{th}$ bin, and $n_i$ is the number of forecasts made within each bin.

Brier Skill Score

It is difficult to use the Brier score to compare different forecasts if the data has a very low baseline rate of events (low uncertainty); simply forecasting lower probabilities can greatly improve the Brier score. Additionally, it has been shown that the naive approach of always forecasting a constant, small probability (the baseline rate of seizures) gives impressive Brier scores due to the rarity of seizures (Schelter et al., 2011b). For this reason, the Brier skill score was used to provide a relative measure for performance comparison. The Brier skill score is computed as $$BSS = 1 - \frac{BS}{BS_{ref}},$$

where BS and $BS_{ref}$ are the Brier scores for a given forecast and some reference forecast. The Brier skill score measures improvement over a reference (where 1 is perfect, 0 shows no improvement, and negative values indicate worse performance than the reference).

To explicitly evaluate the forecast based on an historical record of seizure times, the Brier score was derived from surrogate forecasts as a reference. Surrogate forecasts were constructed for each model by randomly drawing probabilities from the same distribution as the actual forecast made by that model. In this way, 1000 surrogate forecasts were generated to find the mean Brier skill score for each model (combined temporal logistic regression 116, logistic regression only 112, and temporal only 114). The use of forecast surrogates handles the difficulty of comparing forecasts to the constant baseline model, as any constant forecast has a Brier skill score of zero.

Reliability Curves

The reliability curve is a useful visualization tool for the Brier score components, showing a plot of the forecast seizure rate versus the actual seizure occurrence rate. Actual seizure rate was determined by how often a seizure occurred in the pre-ictal period following every forecast. An ideal reliability curve is a diagonal line where forecast probabilities are equal to the actual outcomes.

Seizure Prediction

To validate the utility of the temporally-weighted logistic regression model 112 in a predictive setting, performance was also evaluated using the same metrics that were used for the NeuroVista device trial, referenced previously above. To calculate these statistics, it was necessary to set an upper (lower) probability threshold to trigger a high (low) seizure likelihood advisory period. The same threshold trigger scheme described by (Cook et al., 2013) was used and the process was based on that described in (Snyder et al., 2008), referenced above. For the range of possible high risk thresholds, the amount of time spent in warning, $t_w$, was calculated along with the sensitivity, $S(t_w)$, and sensitivity improvement-over-chance, $S(t_w)-S_C(t_w)$, where $S_C(t_w)$ is the sensitivity of a time-matched chance. These assessment metrics can be mathematically related to the seizure prediction characteristic outlined by Winterhalder et al., "*The seizure prediction characteristic: a general framework to assess and compare seizure prediction methods.*", Epilepsy & Behavior 2003; 4(3): 318-25, the contents of which is hereby incorporated by reference in its entirety. Sensitivity improvement-over-chance compares the accuracy of a predictor to the performance of a time-matched chance prediction (based on a Poisson process), thereby penalizing methods which predict a seizure for a high percentage of time. $S_C(t_w)$ is given by $$S_C = 1 - \exp(-\lambda_w \tau_w + (1 - e^{\lambda_w \tau_{w_0}})) \qquad (8)$$

where $\tau_{w_0}$=5 minutes, $\tau_w$ was set to 40 minutes for the high risk seizure indicator and tuned (between 30 and 60 minutes) for the low risk seizure indicator so that no seizures occurred within the safety advisory period (based on assessment of the pre-seizure data during the algorithm design phase from day 100 to day 200), and $\lambda_w$ is the Poisson rate parameter given by:

$$\lambda_w = -\frac{1}{\tau_w}\log(1 - t_W) \qquad (9)$$

and $t_W$ is the percentage of time spent in the high risk warning phase.

The p-values for the hypothesis that 'the sensitivity is significantly better than chance performance', were also calculated for the sensitivity improvement-over-chance metric. The p-value of the sensitivity improvement-over-chance can be calculated as:

$$p = \begin{cases} 1 - F_B(n-1, N, S_C) + F_B(k, N, S_C), & S \geq S_C \\ 1 - F_B(k, N, S_C) + F_B(n, N, S_C), & S < S_C \end{cases} \qquad (10)$$

where the forecast correctly identifies n out of a total of N seizures, $$S = \frac{n}{N}$$

is the sensitivity, $S_C$ is the sensitivity improvement-over-chance, $k=2NS_C-n$, and $F_B$ is the binomial cumulative distribution function (binocdf in MATLAB).

For the low-risk threshold, the prediction horizon (between 30-60 minutes) and threshold were tuned so that no seizures would occur within the resultant safety advisory period (measured during the 100-day training phase 106). The remaining data 108 was then used to evaluate the time spent in safety, $t_s$, and the number of seizures that occurred during the safety advisory.

It is noted that prediction sensitivity was calculated for lead seizures only. All seizures were used to evaluate the rate of false negatives.

Results

The following is a discussion of the results of the above described performance assessment performed in respect of all three models 112, 114, 116 described above.

Circadian Profiles

Figure 3:
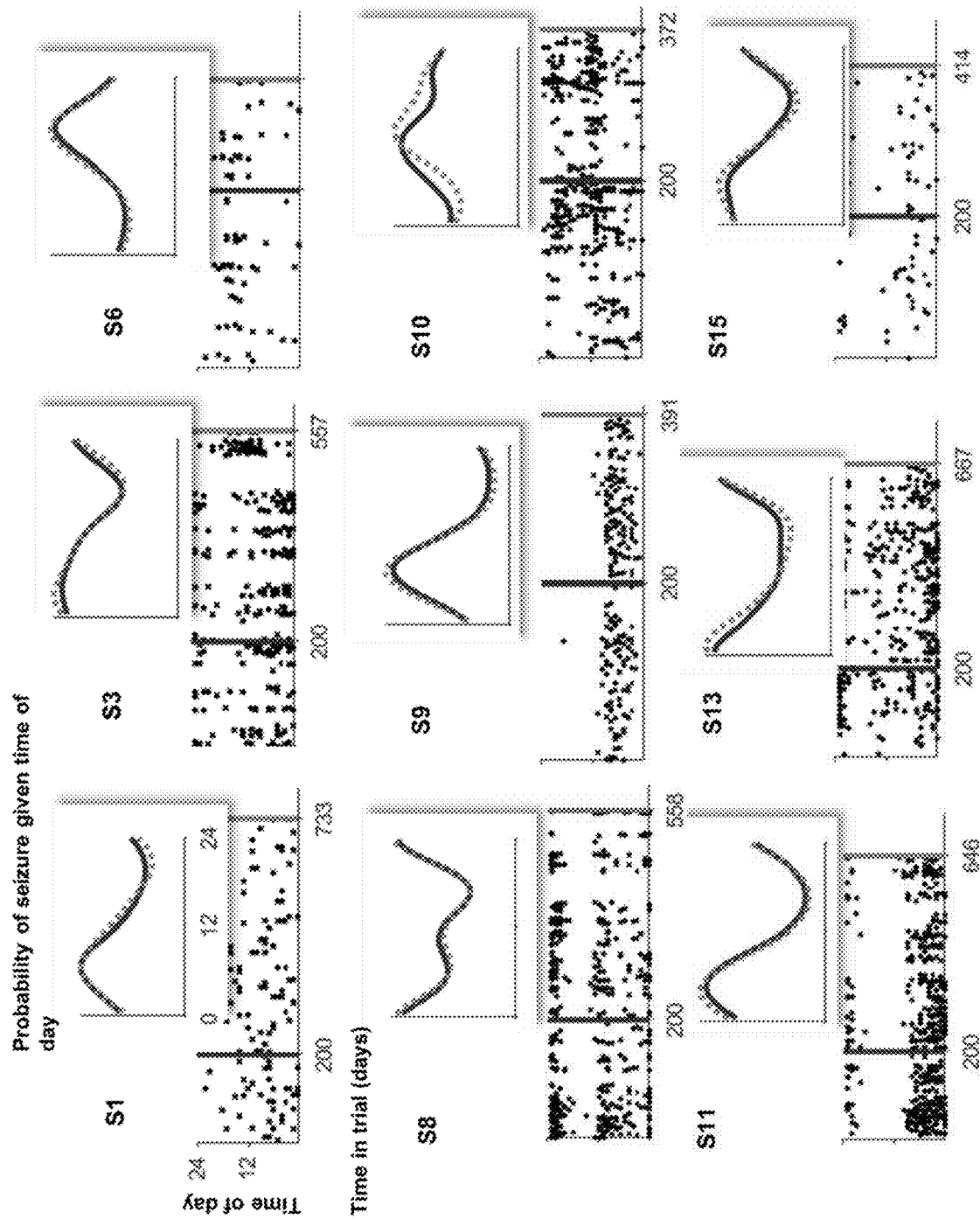
FIG. 3 shows raster plots of seizures experience by nine subjects with respect to time of day together with temporal probability distributions constructed using embodiments of the present disclosure.

FIG. 3 shows raster plots of each of nine subjects' seizures with respect to time of day (i.e. during a circadian cycle), as well as the temporal (circadian) probability distributions constructed from seizure time of day information from the training period 106. The probability distribution curve is shown as a solid line, along with the actual temporal distribution of seizures (broken line). The vertical lines in the raster plots denote the start and end of the training period 106 used to generate the temporal probability distributions for each subject. The circadian distribution (probability of seizure with respect to time of day) was initialized after the hundred-day training period 106 and then updated every time a seizure was observed. FIG. 3 shows the initial (after training) and final (at the completion of the trial) estimates of the probability of a seizure at a particular time of day. Whilst the probability function was updated after every seizure for each subject, the 100 day training period 106 was sufficient in itself to obtain an excellent approximation of the circadian profile. The stability of the seizure probability curves demonstrates that reliable prior information can be obtained after a relatively short training period.

Classifier Training and Validation

Figures 4, 5:
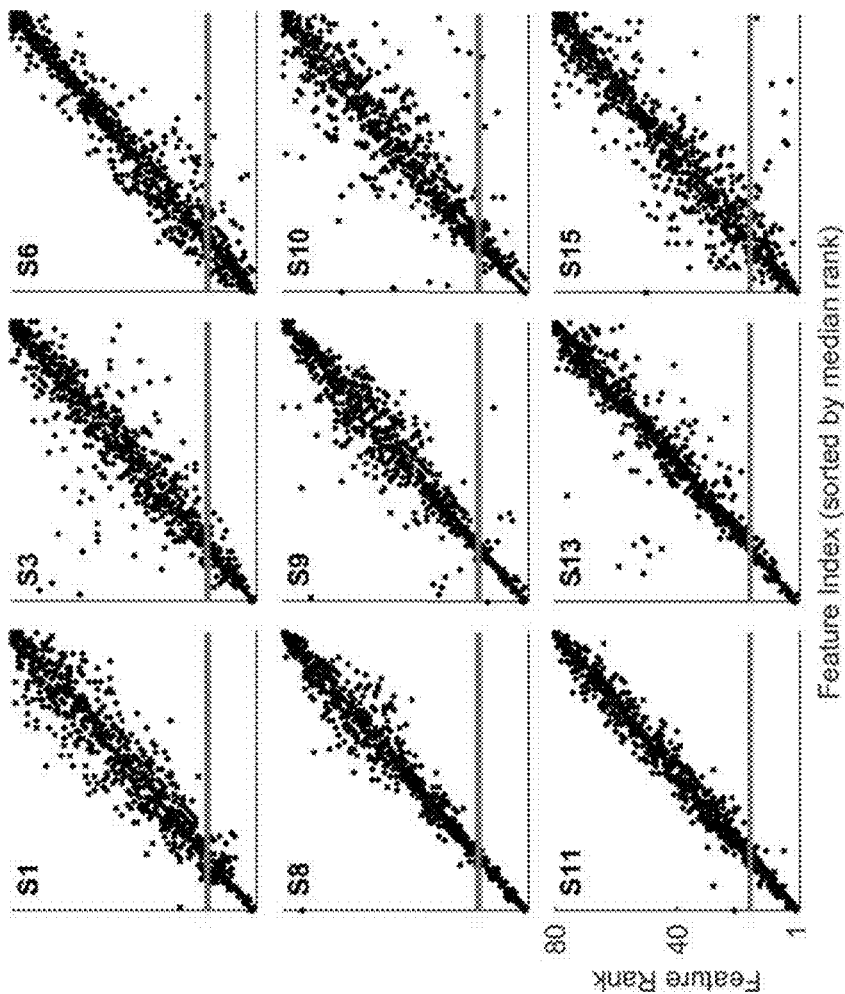
FIG. 4 is a table showing the average area-under-curve (AUC) for each of nine subjects calculated based on true-positive and false-negative pre-ictal detection rate using the temporal logistic regression model shown in FIG. 1.
FIG. 5 shows scatter plots of feature rank against feature index for the nine subjects.

The average AUC for each subject, calculated based on the true positive and false positive pre-ictal detection rate after ten-fold cross-validation, is shown in FIG. 4. All subjects had AUC performance above chance (note that the AUC for chance performance is 0.5, and a perfect score is 1). The average AUC across the nine subjects was 0.79, and two of the subjects had an AUC of 0.90. Reasonable baseline performance with logistic regression classifiers was necessary to demonstrate that improvements using time of day were not trivial.

Figure 6:
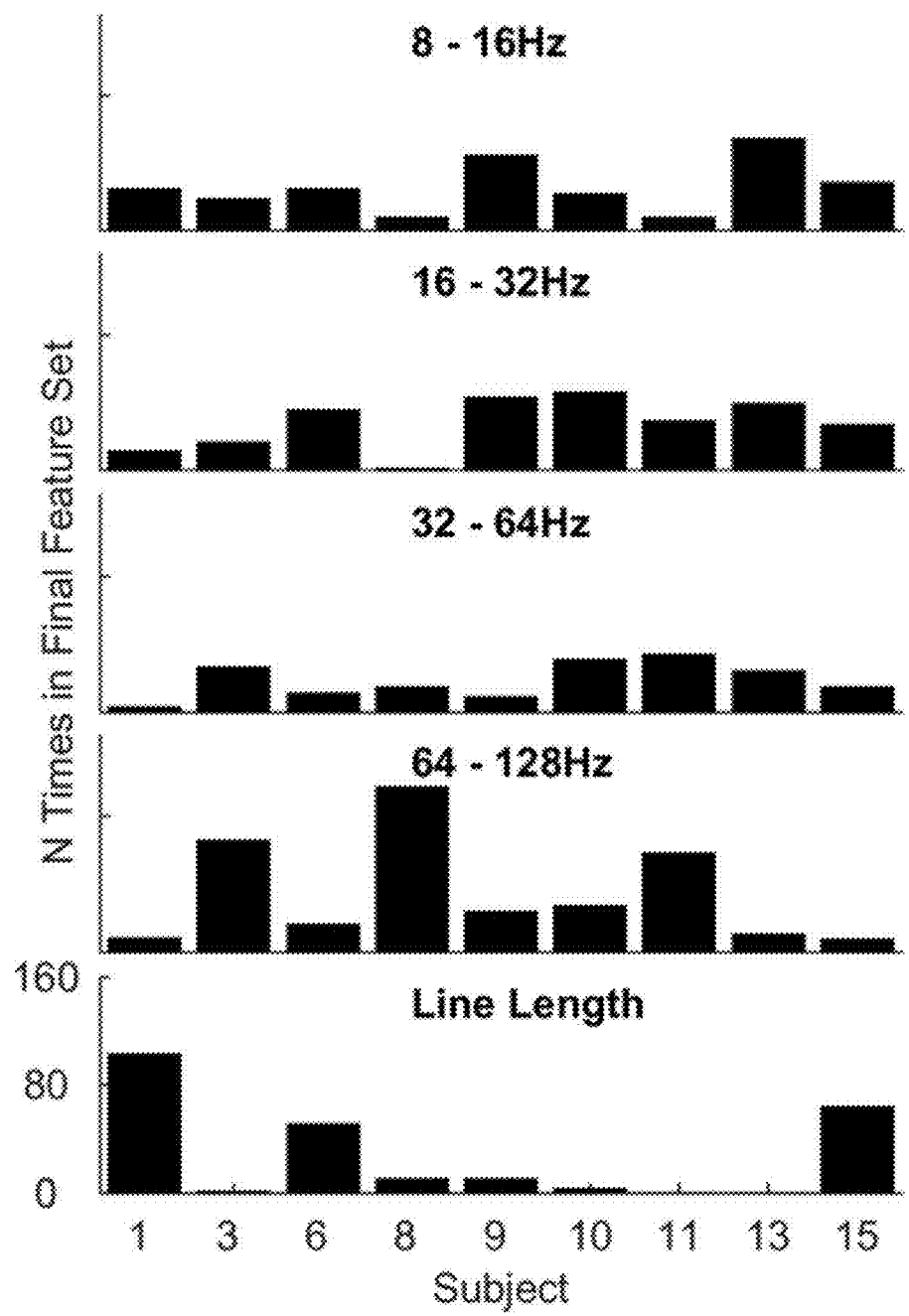
FIG. 6 depicts five histograms illustrating the number of times a feature appeared in each feature set for each of the nine subjects.

As illustrated by FIGS. 5 and 6, it was found that the final features selected for the classifiers were relatively stable across the 10 folds of cross-validation, although the most important features varied between subjects. The scatter plots show in FIG. 5 are tightly distributed around the diagonal, indicating that feature rank did not change dramatically across different validation subsets of data (note that a perfect diagonal line would represent no change in feature rank). Feature stability over time is important for stable classification accuracy. As illustrated in FIG. 6, feature relevance was inferred based on how many times each feature appeared in the final subset of 16 features. Note that as there were 16 recording electrodes, and 10 folds of cross-validation the maximal number of times a feature could appear in the final subset was 10×16=160. Line length and high frequency (64-128 Hz) were highly relevant for six out of the nine subjects (Subjects 1,6, and 15 for line length, and Subjects 3,8, and 11 for high frequency energy). The energy in the lower frequency bands were more evenly distributed in terms of their importance to prediction.

Seizure Forecasting

Figure 7:
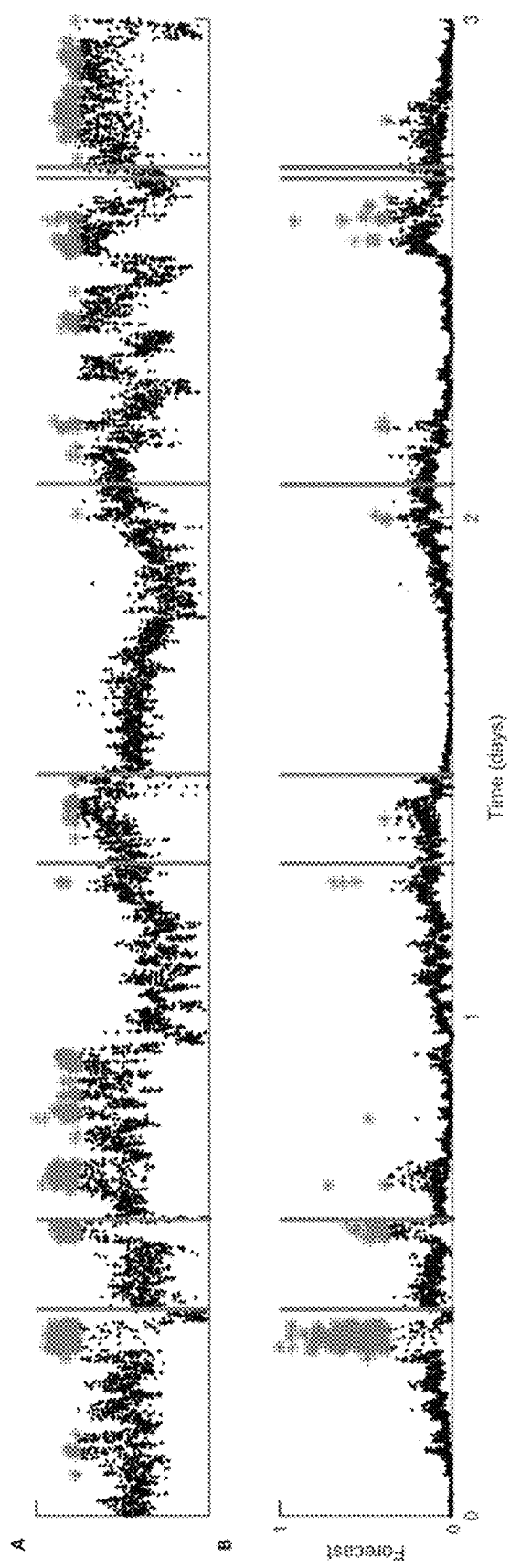
FIG. 7 shows an example output of a logistic regression model (panel A) and the temporal logistic regression model shown in FIG. 1 (panel B) over a 72-hour period.

Forecasts and predictions in the prospective case were performed using the entire remaining day after day 200, i.e. the first day of the remaining period 108. FIG. 7 shows an example output of the logistic regression model (panel A, top) and the combined temporal logistic regression model (panel B, bottom) over a 72-hour period. Forecasts were made every 30 seconds (black dots), and an example prediction threshold is shown at the $95^{th}$ percentile for each model (grey stars); although during later prediction analyses all thresholds were evaluated. Seizures are marked by vertical lines in the plots. It can be seen that the combined temporal logistic regression model (panel B) reduces the number of erroneous threshold crossings into the high risk threshold.

Figure 8:
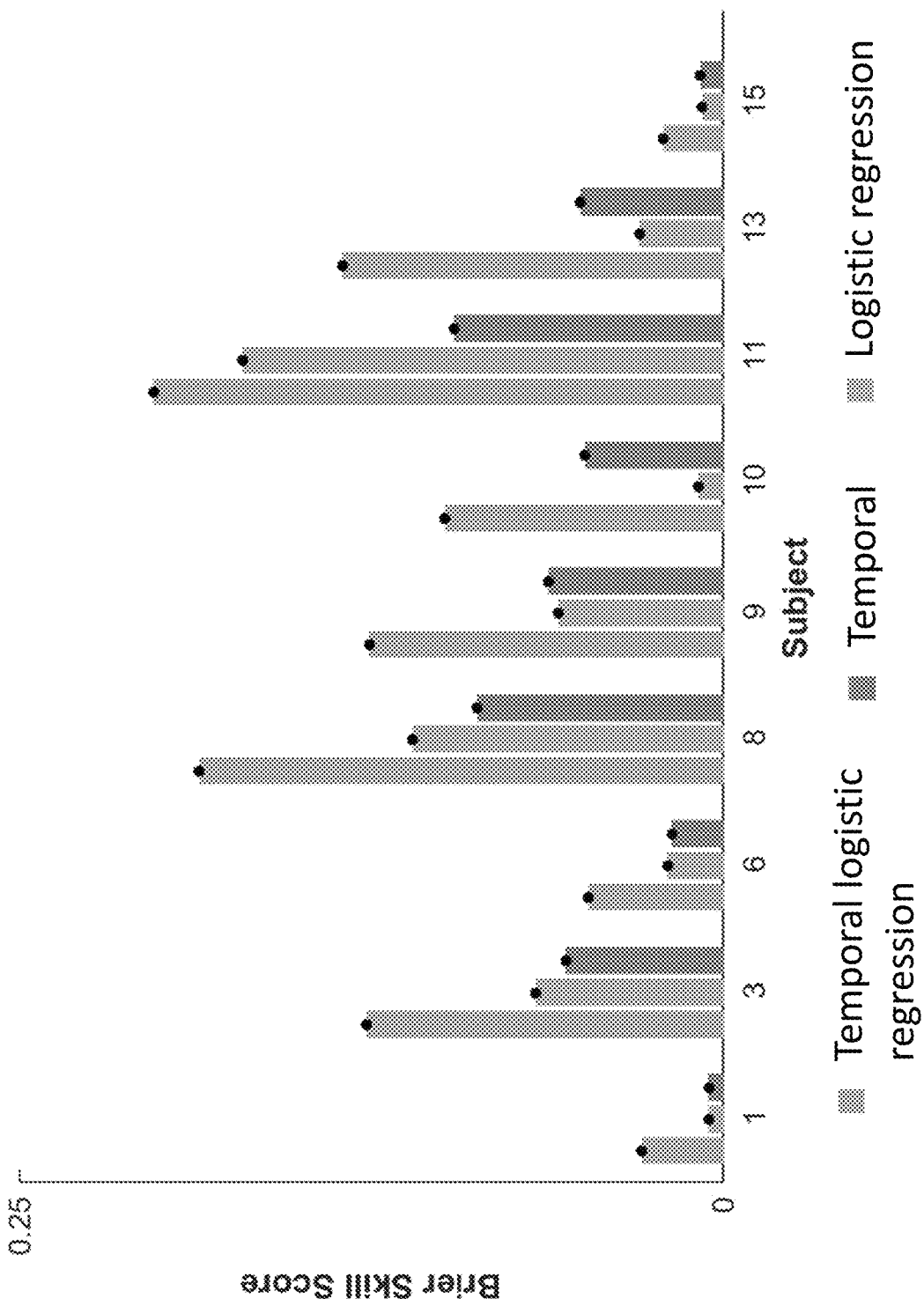
FIG. 8 is a histogram showing Brier scores for each of a temporal model, a logistic regression model and a temporal logistic regression model for each of the nine subjects.

The Brier skill score (mean and standard error) calculated from every forecast made by the three different models 112, 114, 116 is given in FIG. 8. The maximum possible score is 1. For all subjects the combined temporal logistic regression showed the most improvement compared to surrogate data, and significantly outperformed all other models. All forecasting models performed better than the naïve constant baseline forecast, which would give a Brier skill score of 0.

Figure 9:
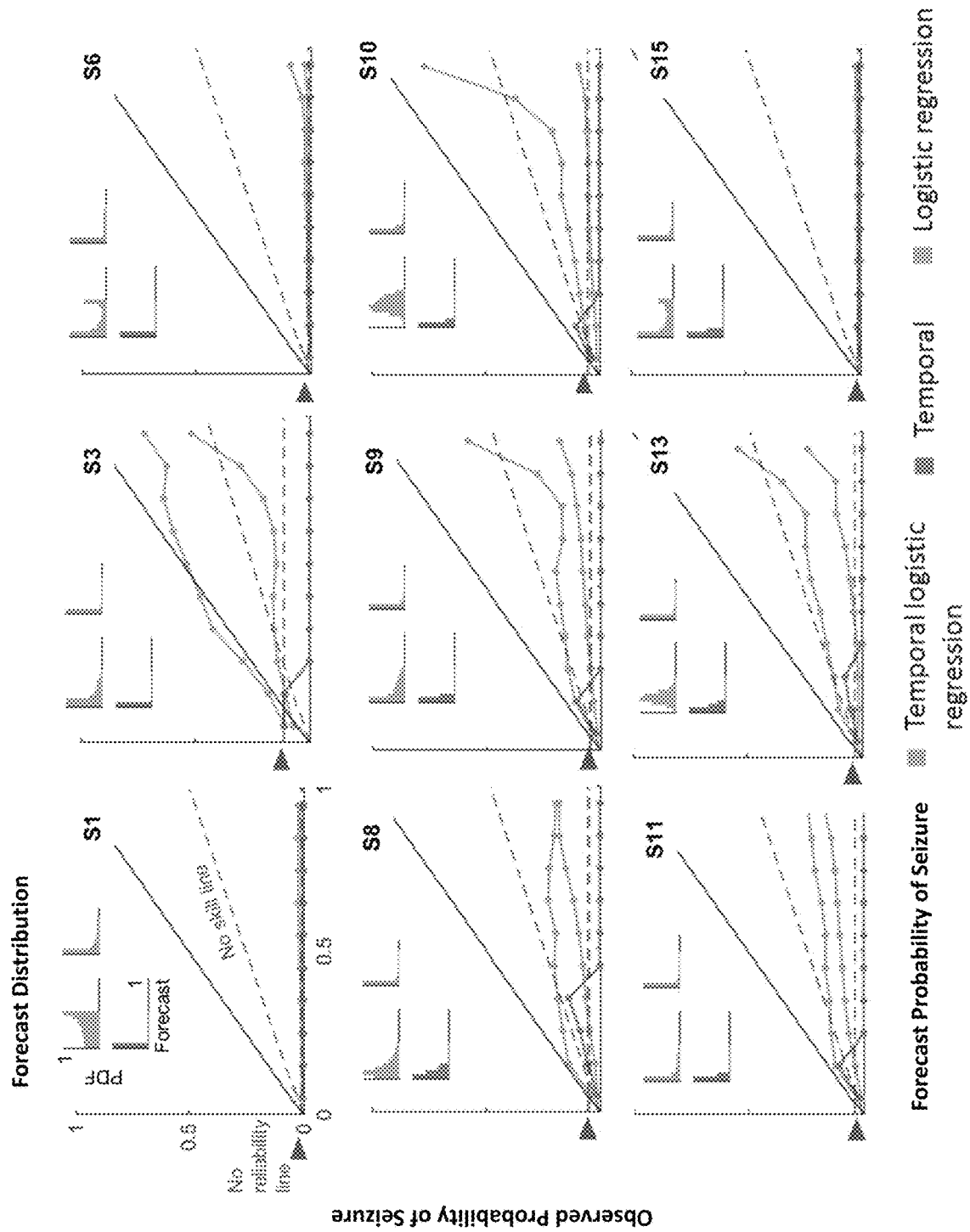
FIG. 9 shows reliability curves for each forecast for each of a temporal model, a logistic regression model and a temporal logistic regression model, for each of the nine subjects.

FIG. 9 shows the reliability curves of each forecast. A perfectly calibrated forecast is a diagonal line (where forecast probability is equal to actual probability). Also shown in the figure is the line of no-reliability (marked by a black arrow in each plot—equivalent to the calibration levels of a constant baseline forecast), and the line of no-skill (diagonal broken line—the point where the Brier skill score is not higher than the constant baseline forecast). Forecasts above the no-reliability (no-skill) line show improved calibration (skill) compared to the constant baseline forecast. FIG. 9 also shows forecast histograms, inset, which are used as a measure of sharpness (how many forecasts are made at different levels of seizure likelihood). It is noted that the temporal only forecast makes no predictions for high probability values. This reflects the fact that a cyclic forecast is not capable of providing good calibration for rare events, and the intuition that forecasts need to outperform a repetitive model to be clinically useful.

For the avoidance of doubt, the fact that forecasts were predominately below the no-skill line does not demonstrate that the forecasting models are poor. In fact, the no-skill line highlights the difficulty of evaluating forecasts for very rare events, since the baseline constant forecast (a model that always predicts a very low chance of seizure) is a close match to reality, and provides reasonable forecasting skill despite having no practical utility for patients. The Brier skill score addressed this challenge, showing improvements above the constant forecast for all subjects, especially for the combined temporal logistic regression model (see FIG. 8).

In addition, most subjects outperformed a constant forecast in terms of reliability (exceptions were Subjects 1, 6 and 15). Subject 3 shows high forecasting skill, and Subjects 9, 10, and 13 show some skill within the high likelihood of seizure regime. Furthermore, the combined temporal logistic regression model (blue line) has superior calibration (closer to diagonal) for all subjects, except subjects 1, 6, and 15.

It can also be seen from the inset histograms in FIG. 9 that the combined temporal logistic regression forecasts were more heavily skewed towards low probability of seizure. We also note that the very poor performers (Subjects 1, 6 and 15) all had logistic regression models that were skewed towards higher probability of seizures (inset histograms, FIG. 9), indicating that performance was compromised by false positives.

It is also important to make note of several points about these subjects. Subject 1 had a highly unusual medication regime. During the initial four-month algorithm design phase (during which no warning lights were enabled), the subject experienced an average of 10 seizures per month. Following this period, the algorithm and warning lights were enabled. During the subsequent 20-month period, in accordance with the investigators directions and in addition to their normal medications, the subject took medications in response to activation of the warning light. During this recording period, the subject experienced significantly fewer seizures, with an average of 5.2 seizures per month ($p<0.01$ using a Wilcoxon rank sum test). Therefore, for Subject 1, results may be confounded by false positives (seizures that were forestalled by medication). Subject 6 was not included in the (Cook et al., 2013) trial due to insufficient performance during algorithm cross-validation. Subject 15 had low seizure numbers and spent a relatively high proportion of time in warning, in both the current and previous study.

FIG. 10 is a table showing prediction performance and results from the Cook et. al trail (2013) with the sensitivity for the combined temporal logistic regression model 116, Logistic regression 112 only, and temporal 114 only forecasts. The number of test seizures listed are those having a preceding seizure-free interval of at least five hours. Prediction sensitivity values are representative of true positive rates, and false negative rates are represented by the number of seizures that occur during safety advisory periods. The times in warning and safety advisory periods are reported in lieu of the false positive rate and true negative rate, as rates are considered less useful than time in warning for evaluating seizure prediction devices. The highest sensitivity is underline for each subject.

It can be seen from the data shown in FIG. 10 that the sensitivity of the new models was equal to or greater than the original trial for all subjects, except Subject 1. For eight out of nine subjects, the combined circadian logistic regression model showed the highest sensitivity, indicating that prior information based on time of day improved performance.

FIG. 11 shows the time spent in the low-risk advisory phase (note that no seizures occurred during low-risk advisory phase unless indicated by an asterisk). For all subjects, the temporal only 112 or combined temporal logistic regression model 116 provided the most time in the low-risk phase. In the Cook et al. (2013) study, only three of the subjects had this feature enabled. Therefore, it can be concluded that using seizure timing provides new insight into times of safety.

Figure 12:
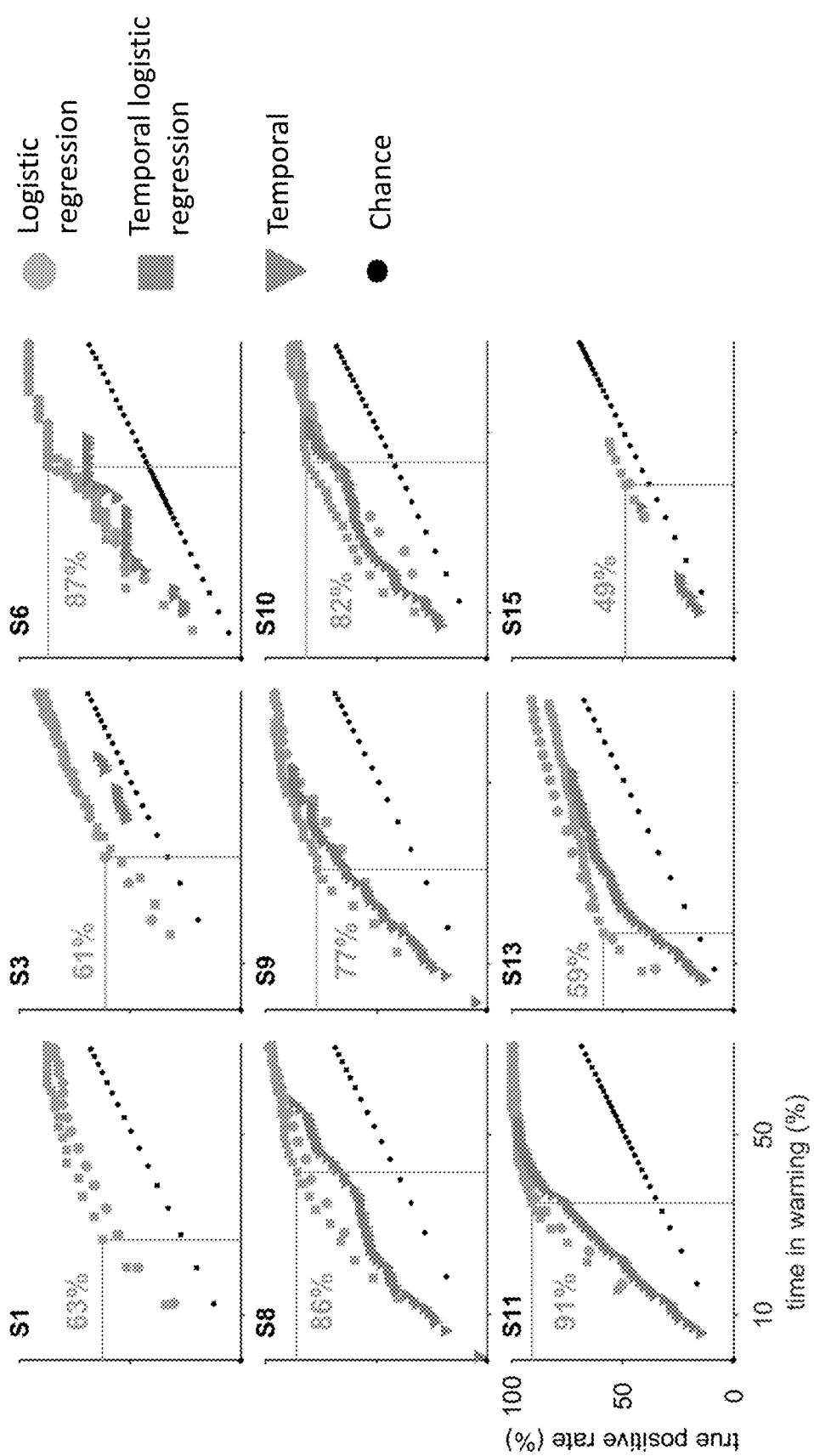
FIG. 12 graphically depicts true positive rate plotted against time spent in warning for each of a temporal logistic regression model, a logistic regression model, and temporal model.

To establish improvement using temporal weighting for a range of operating points, the true positive rate was plotted against the time spent in warning, $t_w$, as shown in FIG. 12. The range of time in warning was obtained by exploring all possible thresholds. In this way, the plotted curves are similar to a receiver operating characteristic curve, but with the time in warning plotted rather than the false positive rate.

The prediction sensitivity was tested at the maximum sensitivity above chance ($S-S_C$) for each subject. These true positive rates ranged from 49% to 91%, demonstrating good prospective performance outcomes for most subjects. The maximum sensitivity was obtained by the combined temporal logistic regression model 116 for all subjects except Subject 3 and Subject 6 (where the logistic regression model 114 had the best performance). Furthermore, for most subjects, the combined temporal logistic regression model 116 has superior performance across the entire operating spectrum of a prospective device (highest curves in FIG. 12). Exceptions are Subject 13, where the combined temporal logistic regression model 116 had the best performance only at the maxima rather than over the entire range.

The above results confirm the predictive benefits of including patient-specific temporal information in a forecasting model for seizures. For most subjects, temporal (particularly circadian) patterns were pronounced and consistent. The embodiments described herein enable arbitrary (patient-specific) temporal patterns to be combined with any form of probabilistic prediction (not limited to logistic regression), and provide noticeable improvements in predictive outcomes for logistic regression classifiers.

It can be seen from these results that the novel methods described herein in which temporal information is included in prediction result in superior forecast and prediction quality compared to purely EEG-based logistic regression, and when compared to the results from the Cook et al. (2013) study. All subjects demonstrated clinical prediction performance significantly better than a chance Poisson prediction (see FIG. 12). Furthermore, the time-matched sensitivity results shown in FIG. 10 demonstrate that the signal features used in the original trial can provide comparable prediction performance over many years (whereas previously reported results were based on a 4-month period).

For all patients, the combined temporal logistic regression model 116 showed superior performance to the logistic regression 114 only and temporal only 112 models in terms of probabilistic measures (Brier skill score and calibration). The combined temporal logistic regression model 116 also provided the best predictive performance for a majority of subjects in a realistic clinical use-scenario. Overall, it has been found that using temporal information improves forecasting accuracy regardless of the precise shape of the temporal distribution, which is highly patient-specific. Furthermore, temporal information provides additional benefits in terms of informing patients of low-risk periods.

The sensitivity performance at the greatest improvement above chance ranged from 49% to 91% (see FIG. 12), demonstrating excellent performance for some subjects. At the original operating points (based on time in warning), the prediction sensitivity ranged from 45% to 76%, higher than compared to previous prediction algorithms on the same dataset (Cook et al., 2013). The low-risk advisory phase was enabled for more patients, and for longer periods with the inclusion of temporal patterns (FIG. 11). Crucially, only one subject had one seizure during their prospective evaluation of the low-risk advisory phase. This result is highly meaningful to patients, as knowing times of safety may sometimes be even more valuable than knowing times of seizure risk. For a majority of subjects, the combined temporal logistic regression model 116 had the best prediction sensitivity across all operating thresholds of a prospective implant device (FIG. 12). This is an important result, as patients have different requirements for device specificity, related to the amount of time that they are prepared to spend in warning. These results show that regardless of how the forecasting model was implemented, time-of-day information improved prediction sensitivity.

Patient-Specific Temporal Cycles

As mentioned above, evidence shows that epilepsy adheres to cyclic pattern which moderate seizures and seizure susceptibility at certain times during these cycles. Due to the ease in monitoring seizures over 24 hour period, in the examples described above, a circadian cycle was chosen as a subject temporal cycle over which to monitor and forecast seizures.

In other embodiments, seizures may be predicted based on the location in time in non-circadian (ultradian or infradian) cycles. Such non-circadian temporal cycles can be used either independently or in combination with other temporal forecasting to accurately forecast the probability of a seizure occurrence at any particular time.

It has been found that the duration of temporal cycles associated with increased seizure probability can be patient specific. In other words, any particular subject may exhibit a temporal seizure probability cycle of arbitrary duration. The duration of such temporal cycles can be determined by analysing historical seizure data for the subject.

Patient data can be analysed to determine the phase and duration of arbitrary (patient-specific) cycles. For each patient, any given seizure time can be expressed as a phase of a cycle with some arbitrary period. The mean resultant length, R, of phase of all seizures for a patient can be determined. The mean resultant length, R, which is the mean phase coherence of an angular distribution, can be calculated using the following equation:

$$R = \frac{1}{N}\sum_{n=1}^{N} e^{i\theta} = 1 - CV$$

where θ is the relative phase, N is the number of samples of the data set, CV denotes the circular variance of an angular distribution obtained by transforming the relative phase angles onto the unit circle in the complex plane. R quantifies the degree of phase locking to a cycle with a particular period. R has values in [0 1], R reaches the value 1 if and only if the condition of strict phase locking is obeyed, i.e. all seizures occur at precisely the same phase of a given cycle (i.e. only at 1 pm for a circadian cycle, or only on day 4 of a 28 day cycle). For a uniform distribution of phases (for example in completely unsynchronized series of seizures) R=0.

FIGS. 13A, 13B and 13C respectively illustrate A) a series of seizures completely unsynchronized with a given cycle (R=0), B) a series of seizures showing 50% synchrony with a given cycle (R=0.5), and C) a series of seizures showing 90% synchrony with a given cycle (R=0.9).

From the above calculation of R with respect to different cycle durations and phases, patient-specific temporal cycles can be determined. FIGS. 14A, 14B and 14C are seizure histograms for respective subjects 11, 7, and 6 referred to above. FIG. 14A shows that subject 11 has a strong circadian seizure cycle, almost all seizures occur between 8 pm and 8 am during a 24 hour (circadian cycle). FIG. 14B shows that subject 7 has a weekly seizure cycle, with most of their seizures occurring on a Friday or a Sunday. FIG. 14C shows that subject 6 has a four-weekly cycle in which no seizures occur in the first week (Week 1) of that four-weekly cycle.

Figure 15:
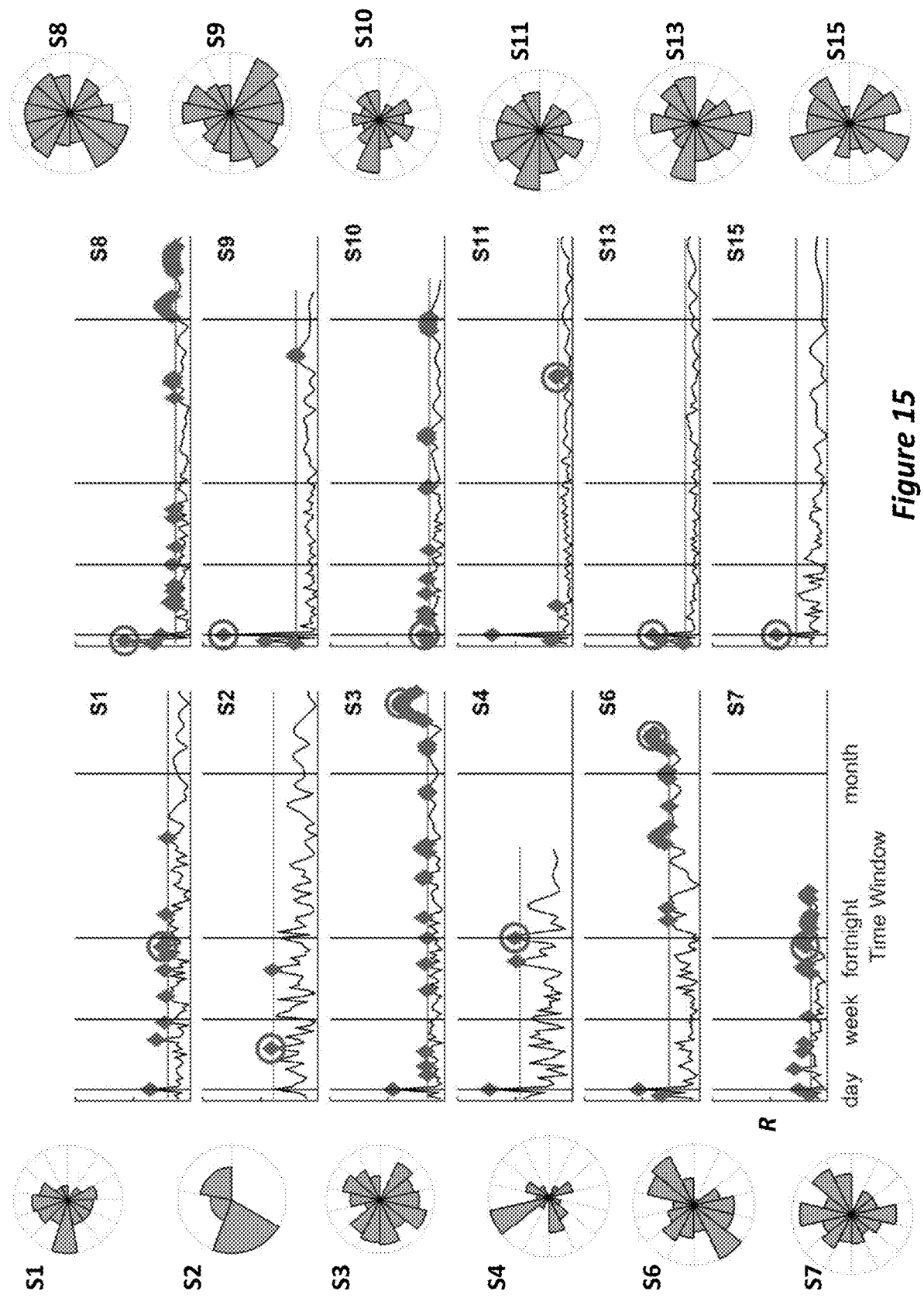
FIG. 15 graphically illustrates the relationship between R-values and cycle duration for day, week, fortnight and monthly cycles for 12 subjects.

The mean resultant lengths, or R-values, were calculated using the method described above for each subject (1, 2, 3, 4, 6, 7, 8, 9, 10, 11, 13, 15) of the Cook et. al trail (2013) listed in FIG. 10 and described above. FIG. 15 graphically illustrates the relationship between R-values and cycle duration for day, week, fortnight and monthly cycles. Each subpanel shows a subject's R value (y-axis) for a given time cycle (x-axis). The presence of significant (non-random) cycles is highlighted by the diamond symbols, the horizontal line denoting p>0.05, corrected for comparisons across multiple time cycles. A statistically significant cycle for each subject (circled in each subpanel) has been presented as a circular histogram (temporal probability distribution) that identifies the peak seizure time.

These results provide further evidence of the value of arbitrary (patient-specific) temporal patterns in forecasting seizures, particularly when combined with any form of probabilistic prediction (not limited to logistic regression), and show that noticeable improvements in predictive outcomes for logistic regression classifiers can be made using such temporal cycles.

It will also be appreciated that multiple different temporal cycles have been identified for some patients. Where multiple temporal cycles are identified for a given subject, seizure probability distributions over each temporal cycle can be combined to provide an improved overall forecast of seizures for that particular subject.

In embodiments described above, a probabilistic model generated using historic physiological data associated with a subject was combined with temporal information to generate a time-weighted probabilistic model taking into account the probability of the subject have a seizure at any particular time of day (or time from a previous seizure). The inventors have realised, however, that in place of or in addition to using a temporal probabilistic model to weight physiological probabilistic models, other data linked to seizure probability may be used to weight such physiological probabilistic models.

Environmental Data

In particular, the inventors have realised that environmental data may also be used to weight probabilistic models generated using physiological data associated with a subject. For example, a correlation has been found between weather conditions and the likelihood of seizures in epilepsy sufferers.

Figure 16:
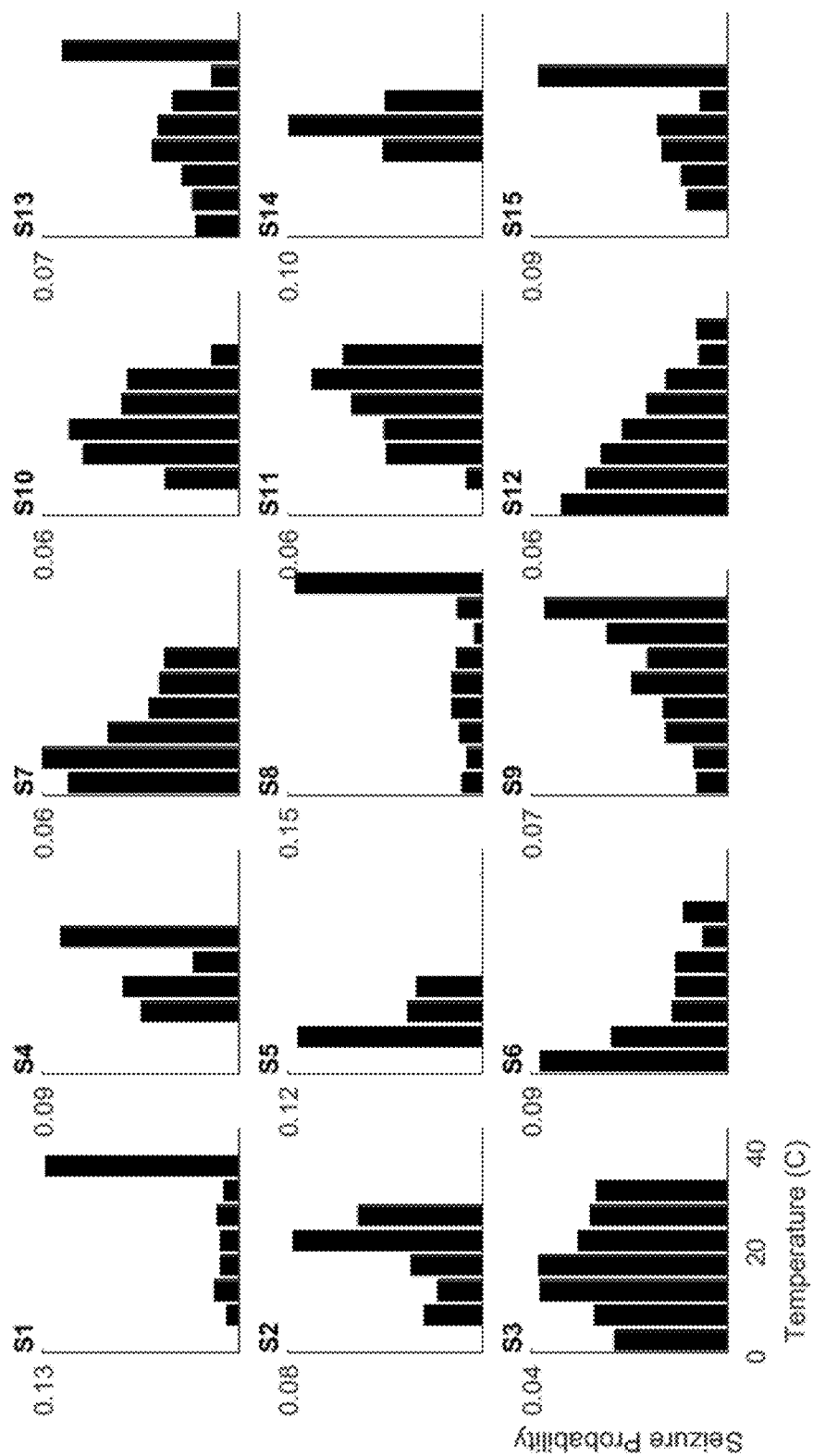
FIG. 16 graphically illustrates the probability of a seizure occurring in fifteen subjects based on air temperature.

FIG. 16 graphically illustrates the probability (or likelihood) of seizure occurrence given air temperature for Melbourne, Australia. Seizure probability one the y-axis is given by the Probability (Seizure|Temperature), i.e. a conditional likelihood of having a seizure given the temperature (x-axis). Each sub-panel shows data generated based on each of the fifteen patients in the NeuroVista trail (referenced above). From these histograms it can be seen that there is a strong relationship between the probability of seizures and temperature, where some patients are sensitive to high temperatures and others are sensitive to low temperatures.

Figure 17:
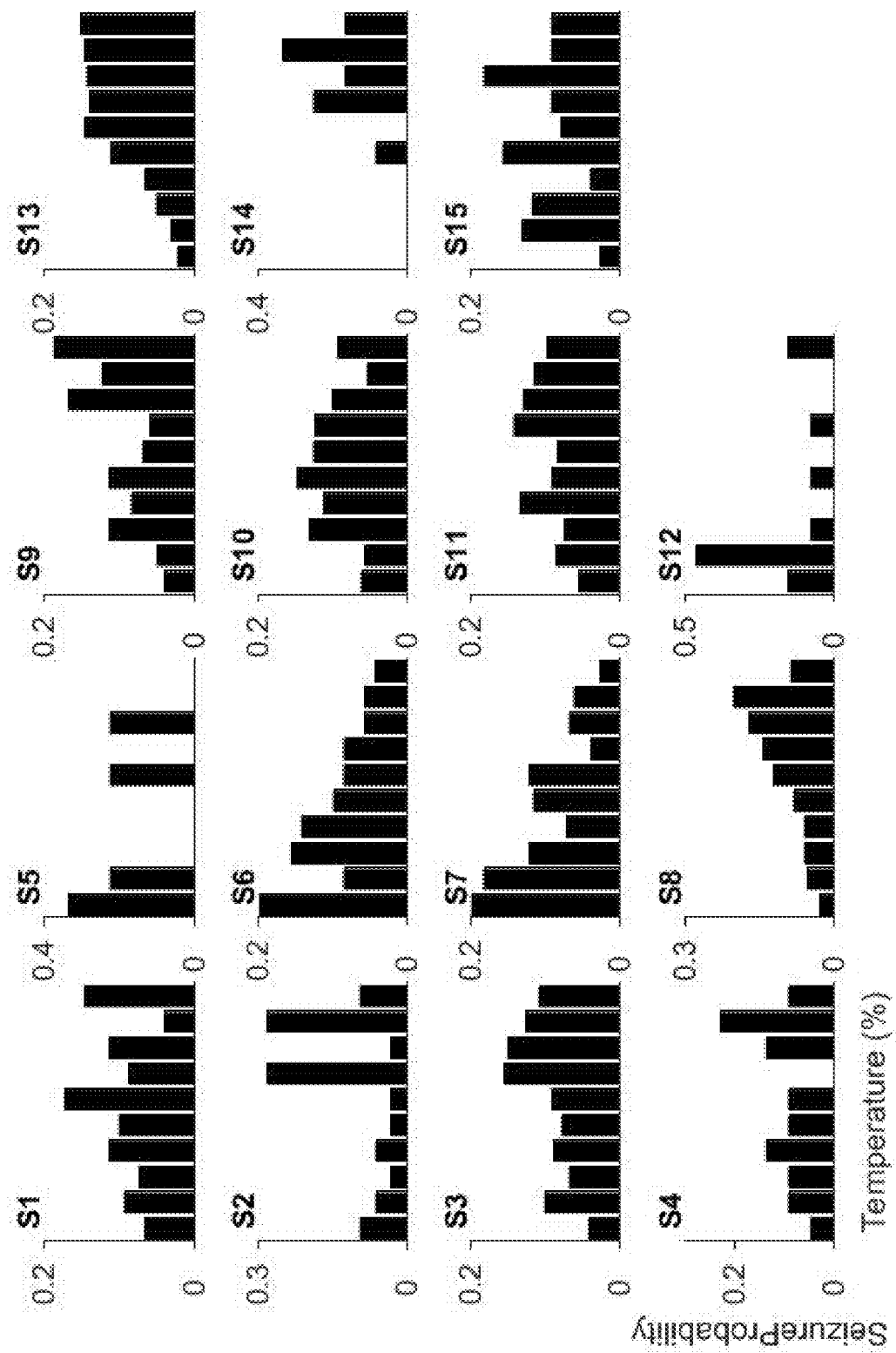
FIG. 17 graphically illustrates the probability of a seizure occurring in fifteen subjects based on air temperature.

FIG. 17 illustrates the probability of seizure occurrence given air temperature for Melbourne, Australia. Each frequency bin contains an equal number of days (first bin being the coldest 10% of days and the last bin representing the warmest 10% of days). Bin edges were calculated based on percentiles (not absolute measurements). Each sub-panel shows data generated based on each of the fifteen patients in the Cook et. al trial (2013) (referenced above). Again, it can be seen that there is a strong relationship between the probability of seizures and temperature, where some patients are sensitive to high temperatures and others are sensitive to low temperatures. For example, it can be seen that subject 13 is more susceptible to seizures during warmer weather, whereas subject 7 is more susceptible to seizures during cooler weather.

Figure 18:
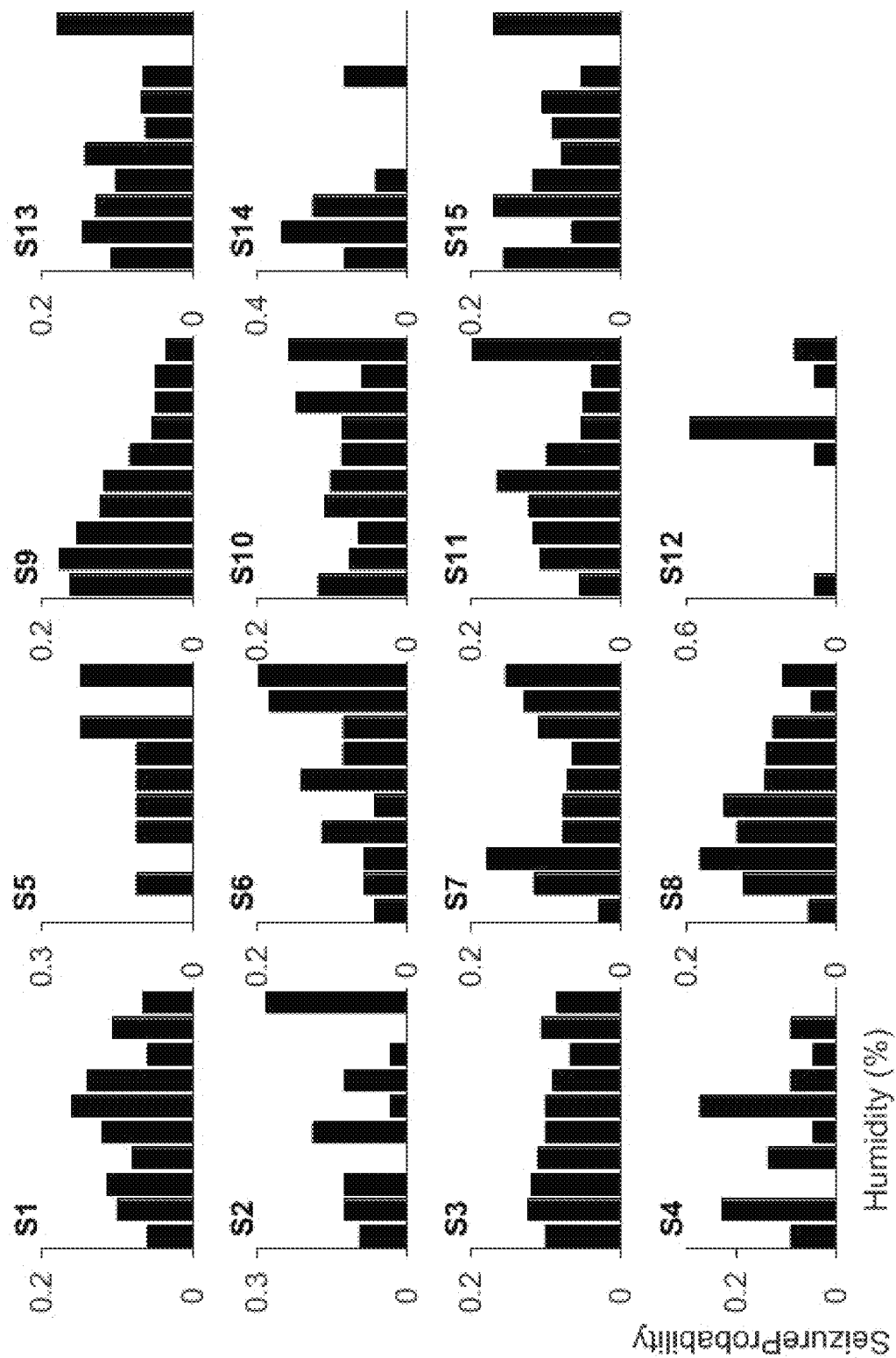
FIG. 18 graphically illustrates the probability of a seizure occurring in fifteen subjects based on humidity.

FIG. 18 illustrates the probability of seizure occurrence given humidity for Melbourne, Australia. Each frequency bin contains an equal number of days (first bin being the least humid 10% of days and the last bin representing the most humid 10% of days). Bin edges were calculated based on percentiles (not absolute measurements). Each sub-panel shows data generated based on each of the fifteen patients in the Cook et. al trial (2013) (referenced above). It can be seen that there are some strong relationships between the probability of seizures and humidity, where some patients are sensitive to high levels of humidity and others are sensitive to low levels of humidity. For example, it can be seen that subject 6 is more susceptible to seizures during higher levels of humidity, whereas subject 8 is more susceptible to seizures during lower levels of humidity.

Figure 19:
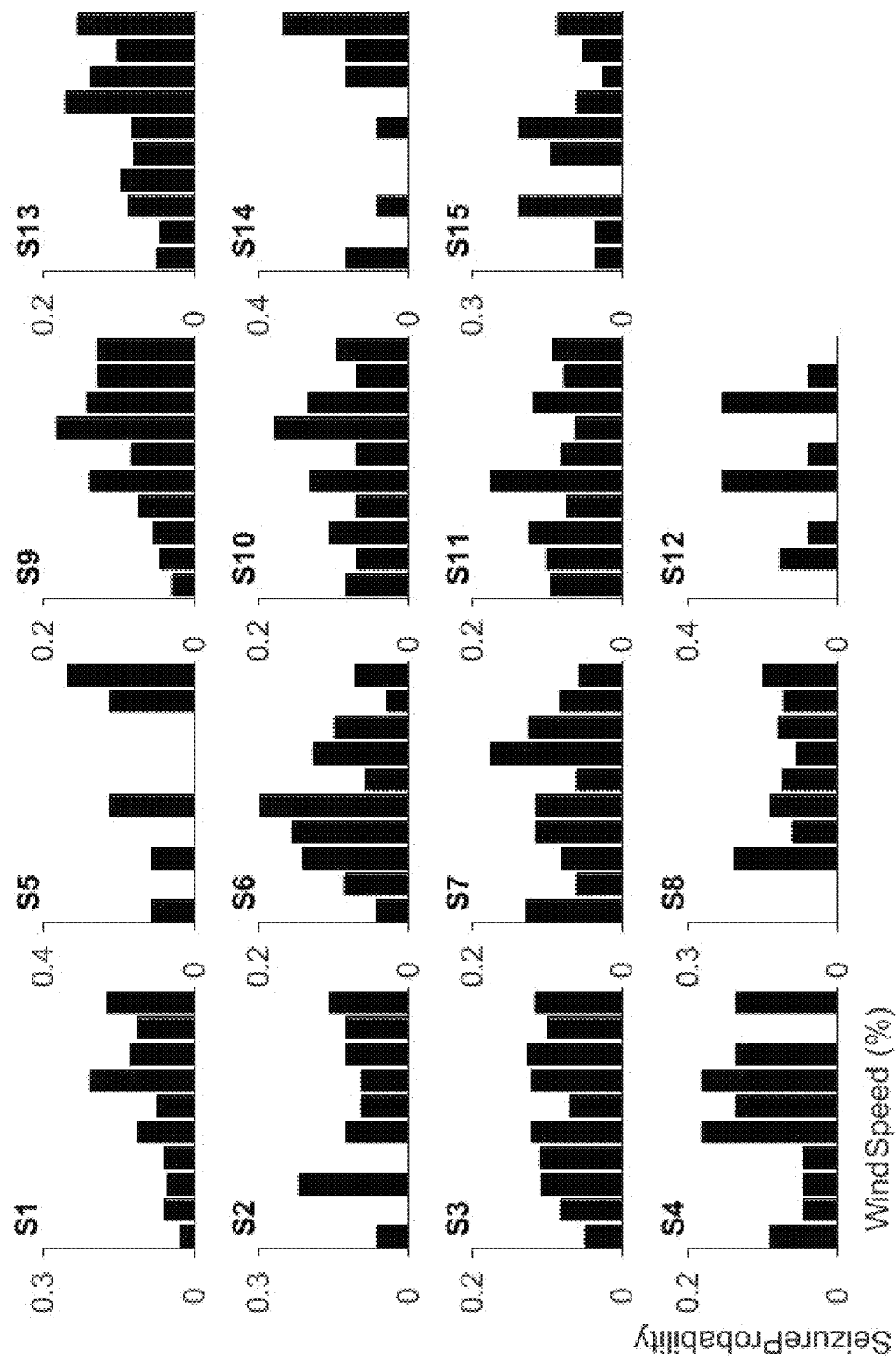
FIG. 19 graphically illustrates the probability of a seizure occurring in fifteen subjects based on wind speed.

FIG. 19 illustrates the probability of seizure occurrence given wind speed for Melbourne, Australia. Each frequency bin contains an equal number of days (first bin being the 10% of days with the lowers wind speeds and the last bin representing the 10% of days having the highest wind speeds). Bin edges were calculated based on percentiles (not absolute measurements). Each sub-panel shows data generated based on each of the fifteen patients in the Cook et. al trial (2013) (referenced above). It can be seen that there are some strong relationships between the probability of seizures and temperature, where some patients are sensitive to high wind speeds and others are sensitive to low wind speeds. For example, it can be seen that subjects 1, 5, 13, and 15 are more susceptible to seizures during periods of high wind speed and subject 6 appears to be more susceptible to seizures during periods of moderate wind speed.

Figure 20:
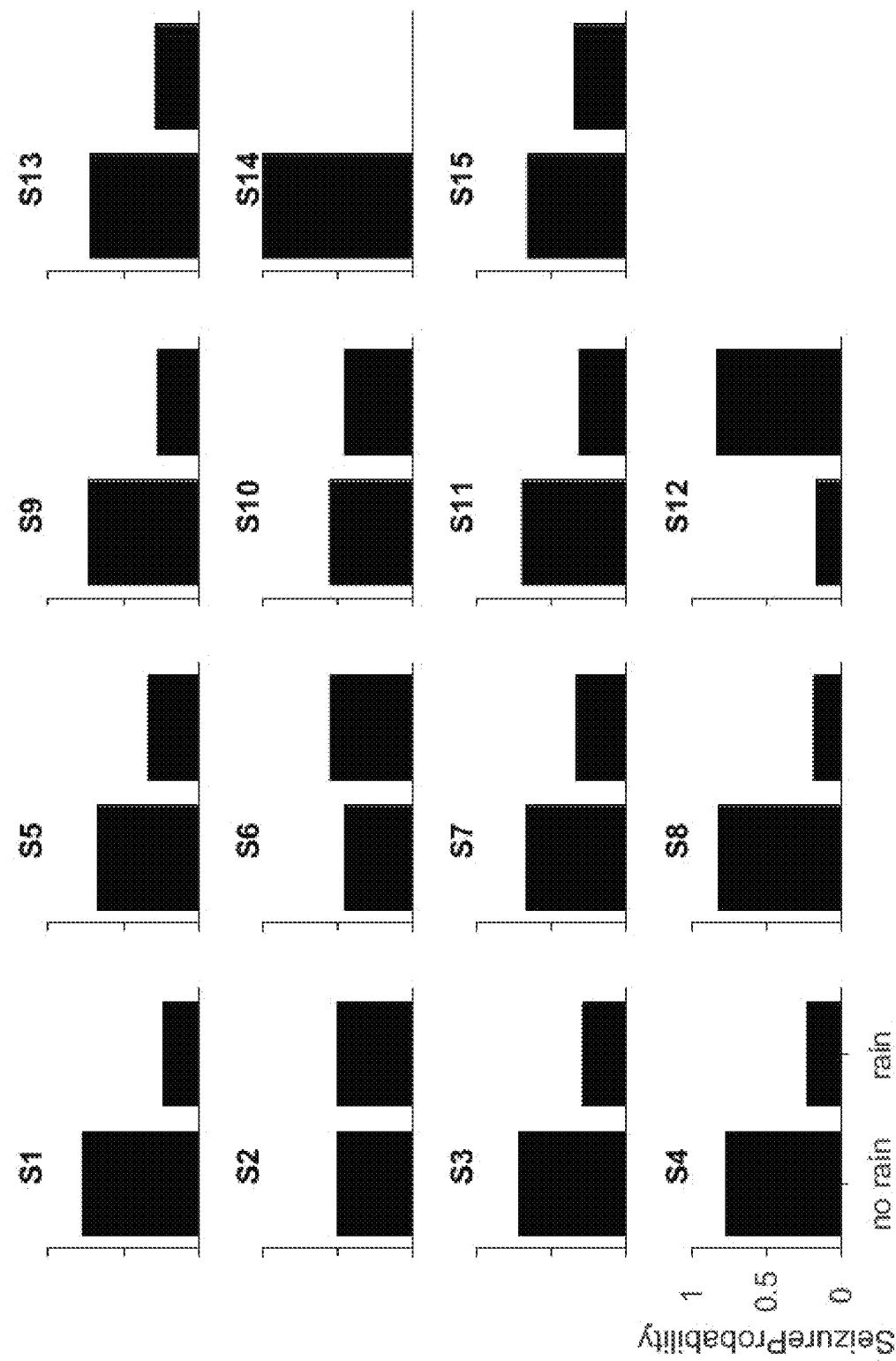
FIG. 20 graphically illustrates the probability of a seizure occurring in fifteen subjects based on rainfall.

FIG. 20 illustrates the probability of seizure occurrence based on instances of rainfall for Melbourne, Australia. Each sub-panel shows data generated based on each of the fifteen patients in the Cook et. al trial (2013) (referenced above). It can be seen that there are some strong relationships between the probability of seizures and rainfall on that particular day, where some patients have a relatively high probability of seizure on days when it rained, some patients have a relatively high probability of seizure when it didn't rain, and some patients have a substantially equal probability of seizure regardless of whether or not it rains on a particular day. For example, it can be seen that subjects 1, 4, 5, 8, 9, 11, 13, 14, and 15 are more susceptible to seizures during periods of no rain, subjects 12 appears to be more susceptible to seizures days of rain and subjects 2, 6 and 10 appear to not be somewhat unaffected by days of rainfall.

Figure 21:
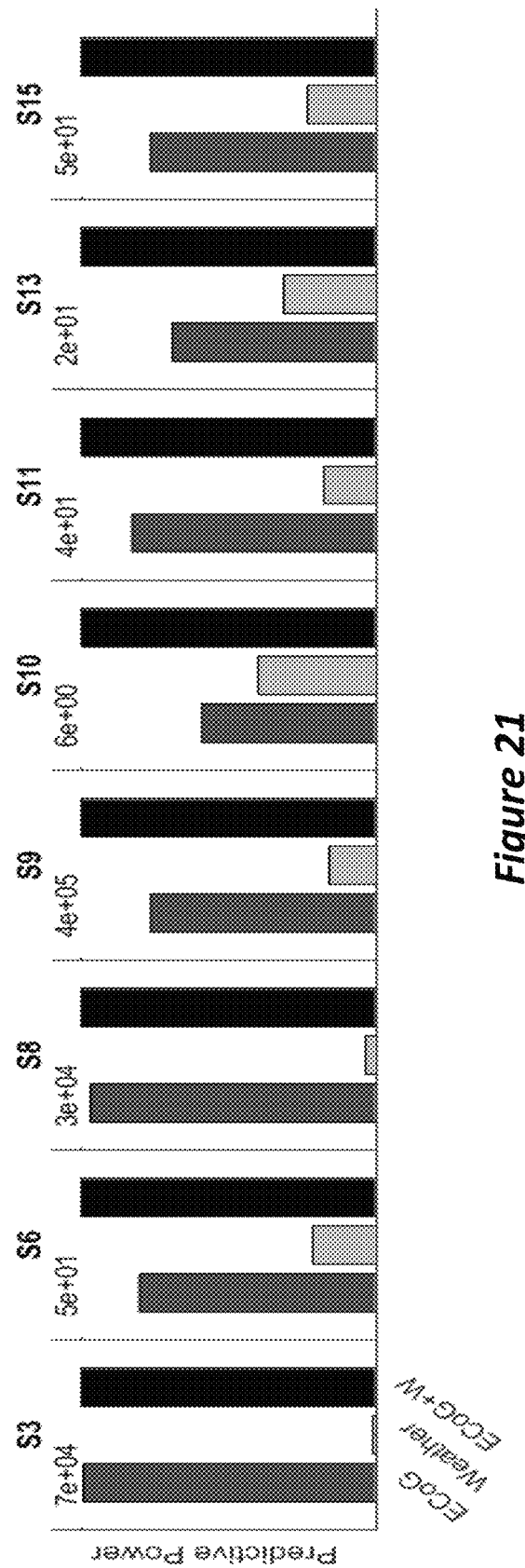
FIG. 21 graphically illustrates the effect of using environmental conditions to forecast seizure probability.

FIG. 21 illustrates the effect of taking into account weather conditions when forecasting seizure probability. Bar graphs are shown for subjects 3, 6, 8, 9, 10, 11, 13, and 15 of the fifteen patients in the Cook et. al trial (2013) (referenced above). Bar heights represent the ratio of probabilities for background (inter-ictal) compared to pre-seizure (pre-ictal) data (where data was 10 minute segments of data sampled from either before seizures (pre-ictal), or away from seizures (inter-ictal)). Higher ratios indicate that pre-ictal data is more distinct from inter-ictal data using the model, suggesting better separability and improved predictive value. In each bar chart, three bars are shown, namely ECoG, weather and the combination of ECoG and weather. ECoG represents seizure probability derived from ECoG signal features (e.g. spikes) only. Weather represents seizure probability derived from environmental data, specifically the Bayesian combination of humidity, temperature, rainfall, and wind speed. The combination of ECoG and weather represents seizure probability derived from the Bayesian combination of ECoG and environmental data. It can be seen that for all seven subjects shown, the addition of environmental consideration increases the predictive power of methods and apparatus described herein.

Accordingly, in some embodiments, methods equivalent to those described above for generating temporal probability distributions may be used to generate subject-specific environmental (e.g. temperature, humidity, wind and/or rain) probability distributions defining relative probability of a subject having a seizure based on the environment (e.g. temperature, humidity, wind and/or rain) at the location of the subject. This environment probability model may then be used to weight a probabilistic model generated using physiological data using an analogous approach to that described above for weighting using temporal probability functions. The environmental probability model may be combined with one or more temporal probability models to further increase the accuracy of forecasting for a particular patient. Combined probability models may be further combined with one or more logistic regression models (or the like) to yet further increase the accuracy of such forecasting.

Sleep Data

The inventors have realised that sleep data may also be used to weight probabilistic models generated using physiological data associated with a subject and/or environmental data. For example, a correlation has been found between features of sleep patterns and the likelihood of seizures in epilepsy sufferers.

Figure 22:
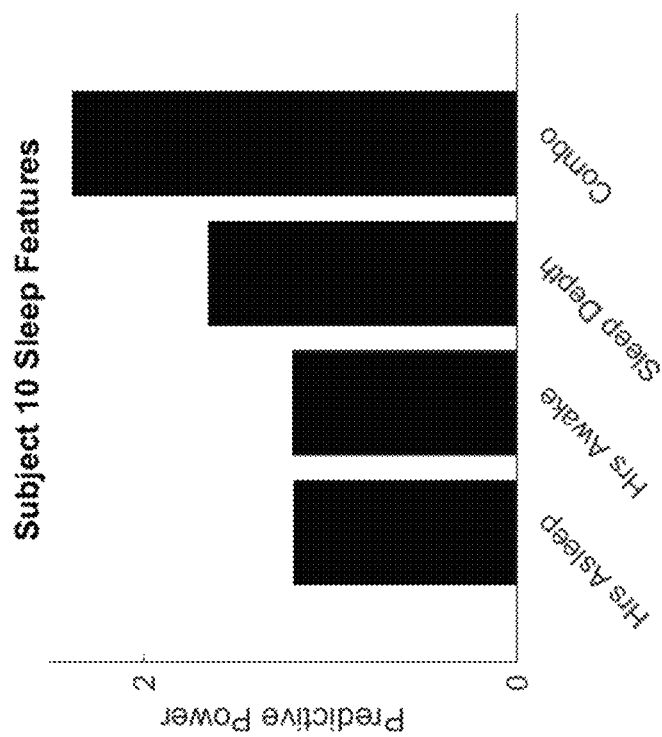
FIG. 22 graphically illustrates the effect of using sleep data to forecast seizure probability.

FIG. 22 illustrates the comparative predictive power of using features of a patient's (subject 10) sleep patterns to forecast seizure probability. Sleep patterns were observed using ECoG and analysed to determine for a patient, over a 24 hour cycle, a) hours asleep, b) hours awake, and c) sleep depth. Bar heights represent the ratio of probabilities for background (inter-ictal) compared to pre-seizure (pre-ictal) data (where data was 10 minute segments of data sampled from either before seizures (pre-ictal), or away from seizures (inter-ictal)). Higher ratios indicate that pre-ictal data is more distinct from inter-ictal data using the model, suggesting better separability and improved predictive value. The predictive power of the combination of all three (a-c) is also shown (labelled "Combo") derived from the Bayesian combination of a-c.

Figure 23:
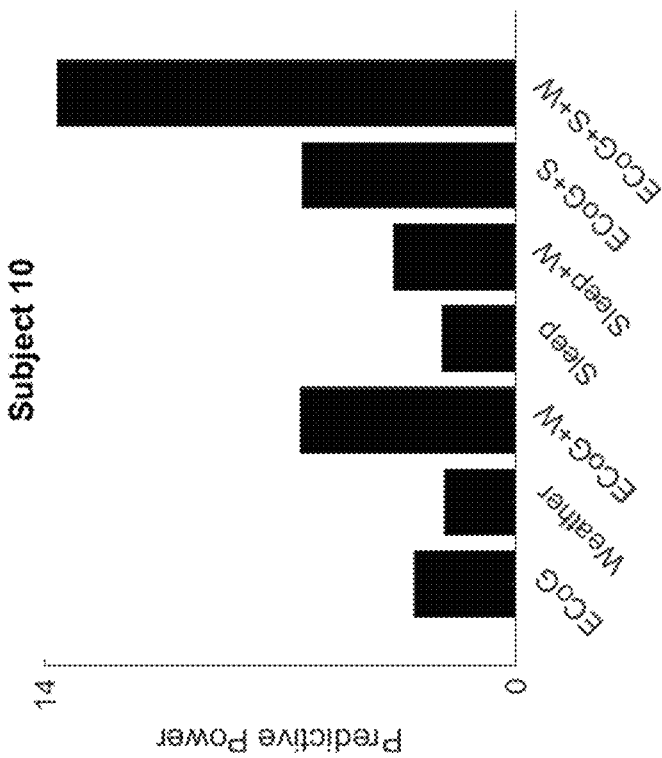
FIG. 23 graphically illustrates the comparative effect of using measured ECoG, weather and sleep data both alone and in combination on seizure forecasting.

FIG. 23 provides a comparison the predictive power of ECoG, weather and the combination of ECoG and weather, sleep, the combination of weather and sleep, the combination of ECoG and sleep, the combination of ECoG, weather and sleep. It can be seen that the use of sleep provided improvements in predictive power when combined with each of ECoG alone and weather alone, as well as when combined with both ECoG and weather.

Accordingly, in some embodiments, methods equivalent to those described above for generating temporal probability distributions may be used to generate subject-specific sleep probability distributions defining relative probability of a subject having a seizure based on a sleep condition of the subject. This sleep probability model may then be used to weight a probabilistic model generated using physiological data using an analogous approach to that described above for weighting using temporal probability functions. The sleep probability model may be combined with one or more temporal probability models and/or one or more environmental probability models to further increase the accuracy of forecasting for a particular patient. Combined probability models may be further combined with one or more logistic regression models (or the like) to yet further increase the accuracy of such forecasting.

Seizure Advisory Systems

Practical applications of the above-described methods will now be described. In particular, the above methods for seizure forecasting may be used by a seizure advisory system to advise subjects of the probability that they will experience a seizure during a particular timeframe. In the embodiments described, systems are provided for recording and processing both physiological information related to epileptic events experienced by a subject and temporal information associated with those events. Probabilistic forecasting such as that described above is also implemented to provide a seizure advisory system which provides subjects with information concerning the prospective likelihood of seizure so that they may take necessary action to forestall such events or make themselves safe before onset of a seizure.

Figure 24:
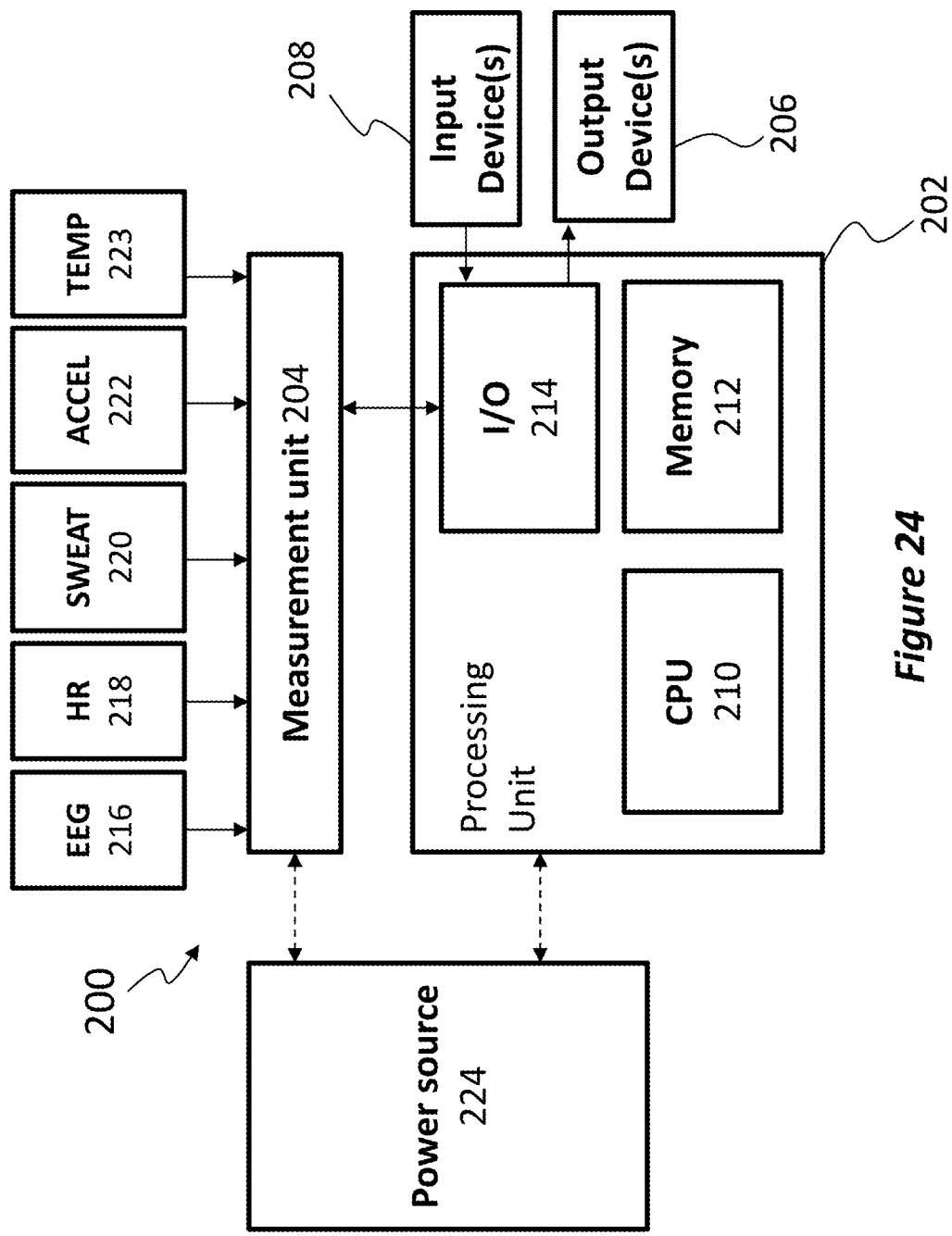
FIG. 24 is a schematic illustration of a seizure advisory system according to embodiments of the disclosure.

An example seizure advisory system 200 according to an embodiment of the disclosure is illustrated in FIG. 24. The system 200 comprises a processing unit 202, a measurement unit 204, one or more output devices 206 and, optionally, one or more input devices 208. The processing unit 202 comprises a central processing unit (CPU) 210, memory 212, and an input/output (I/O) bus 214 communicatively coupled with one or more of the CPU 210 and memory 212.

The measurement unit 204 is coupled to one or more devices for recording physiological data. Measurement devices which may be coupled to the measurement unit 204 may comprise (but are not limited to) an EEG monitoring device 216 a heart rate monitor 218, a sweat sensor 220 an accelerometer 222 (or similar motion detector), and a temperature and/or humidity sensor 223. Other examples of measurement devices which may be coupled to the measurement unit 204 include blood pressure monitors, glucose monitors, cortisol sensor, and gyroscopes etc.

The EEG monitoring device 216 may comprise one or more electrode leads each comprising one or more electrodes. Such leads may be implanted intracranially (intracranial EEG) and/or located external to the head. Leads which are implanted intracranially may be placed on the surface of the brain and/or implanted within the brain tissue. Leads of the EEG monitoring device 216 may be configured, in use, to record neural activity at a neural structure in a brain of the subject.

The measurement unit 204 may comprise one or more amplifiers and/or digital signal processing circuitry for processing signals received from the one or more measurement devices 216, 218, 220, 222, 223. Such signal processing circuitry may include, for example, sampling circuits for sampling signals received from the one or more measurement devices 216, 218, 220, 222, 223 as well as filters for filtering such signals in accordance with embodiments described above. The measurement unit may also be configured to extract and process information received from the one or more measurement devices 216, 218, 220, 222, 223. To that end, the measurement unit 204 may include memory to store data received from the one or more measurement devices 216, 218, 220, 222, 223.

In addition to receiving data from the one or more measurement devices 216, 218, 220, 222, 223, the system 200 may be configured to receive data concerning local weather forecasts or conditions from the internet in any manner known in the art. For example, the system 200 may comprises a wireless modem or other device for connecting to a wired or wireless network (such as a cellular network). The system 200 may then use information received via the wired or wireless network concerning environmental conditions (e.g. temperature, humidity, rainfall, barometric pressure, wind speed etc.) for the forecasting of seizure probability.

Where EEG is utilised for seizure forecasting and prediction, the measurement unit 204 may also be used in conjunction with a signal generator (not shown) to measure electrode impedances. The measurement unit 204 may be external to or integrated within the processing unit 202. Communication between the measurement unit 204 (and/or the signal generator) on the one hand and the I/O bus 214 on the other may be wired or may be via a wireless link, such as over inductive coupling, WiFi®, Bluetooth® or the like. Equally, communication between the measurement unit 204 and the one or more measurement devices 216, 218, 220, 222, 223 may be wired or may be via a wireless link such as those listed above.

Power may be supplied to some or all elements of the system 200 from at least one power source 224. The at least one power source 224 may comprise a battery such that elements of the system 200 can maintain power independent of mains power when implanted into a subject.

In some embodiments, some or all functions of the measurement unit 204 may be implemented using the processing unit 202. In which case, the one or more measurement devices 216, 218, 220, 222, 223 may be coupled directly to the I/O bus 214.

The one or more (optional) input devices 208 may include but are not limited to one or more of a keyboard, mouse, touchpad and touchscreen. Examples of the one or more output devices 206 include displays, touchscreens, light indicators (LEDs), sound generators and haptic generators. Input and/or output devices 208, 206 may be configured to provide feedback (e.g. visual, auditory or haptic feedback) to a subject.

Feedback provided by the one or more output devices 206 may include information concerning seizure likelihood in a subject, particularly a subject to which information recorded by the measurement unit 204 relates. Such information may include one or more of a seizure probability, a seizure risk rating, information concerning the cause of risk elevation (e.g. time of day, weather conditions, etc.). Such information may be portrayed graphically or through the use of auditory or haptic feedback (as discussed above).

The one or more input devices 208 may enable the subject to acknowledge information and feedback provided via the one or more output devices 206 as well as input data into the system 200 which may then be used to improve forecasting of future seizures. This information may include data pertaining to the subject symptoms during a seizure. Such information may be used to verify or refute predictions previously made by the system 200.

To monitor the time of day for the purposes of forecasting seizure likelihood based on the temporal profile of a subject, the processing unit 202 comprises a 12- or 24-hour clock operable to measure time.

The temperature and/or humidity sensor 223 may be provided to monitor temperature and/or humidity for the purpose of forecasting seizure likelihood based on a temperature and/or humidity based probability model associated with a subject.

Figure 25:
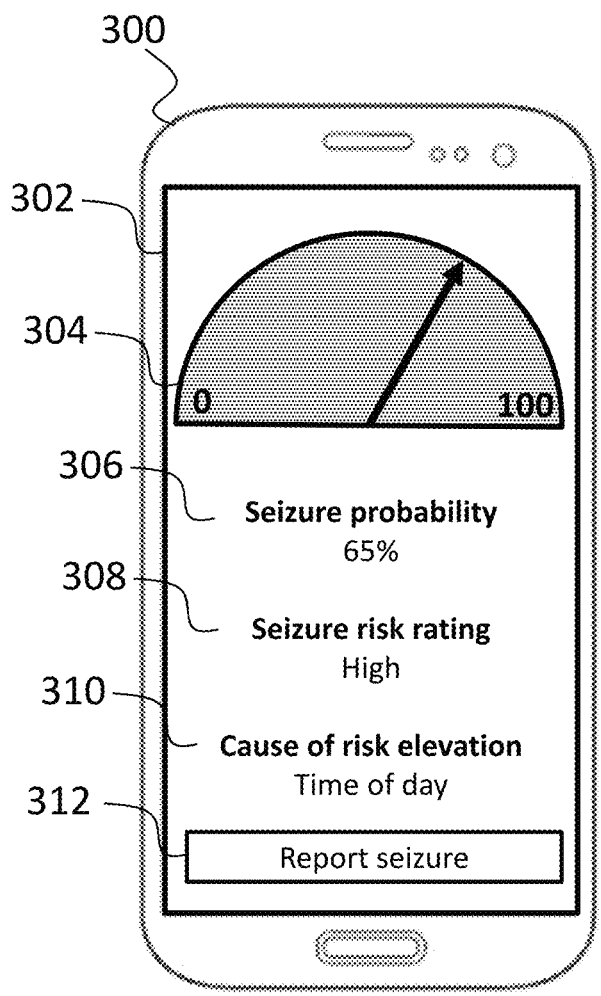
FIG. 25 is a schematic illustration exemplifying the seizure advisory system shown in FIG. 24.

In some embodiments, some or all of the system 200 shown in FIG. 24 may be implemented using a smartphone or similar digital device (tablet, computer etc.). FIG. 25 illustrates an exemplary smartphone device 300 upon which the system 200 may be implemented. The device 300 comprises a touchscreen display 302 which can function as both the input device 208 and output device 206 of FIG. 24. In the embodiment shown in FIG. 25, the touchscreen 302 provides a graphical illustration 304 of the probability of a seizure occurring, together with written information concerning seizure probability 306, a seizure risk rating 308 and information concerning the cause of elevation of risk 310 (as discussed above). In addition, a button 312 is provided on the touchscreen to enable a subject to input data concerning a seizure which has occurred. Auditory warnings may also be playable on the device 300.

In some embodiments, the one or more measurement devices 216, 218, 220, 222, 223 may be coupled to the smartphone 300 via one or more wired or wireless links. In which case, the measurement unit 204 may be implemented using the smartphone 300. Alternatively, the measurement unit 204 may be separate to the smartphone 300. In which case, the measurement unit 204 itself may be wired or wirelessly coupled to the smartphone 300.

As technology for long-term implantable recording devices becomes readily available, the use of individualized temporal prior information and probabilistic metrics can benefit seizure prediction immensely.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method comprising:
receiving historical data associated with epileptic events experienced by the subject over a first time period, the historical data comprising a time at which each epileptic event occurred;
generating a combined temporal probability model of future epileptic events based on the time of each of the epileptic events, the combined temporal probability model representing a time-weighted probability of a future seizure occurrence in each of a plurality of time windows,
wherein the combined temporal probability model is generated by combining two or more probability density functions, each probability density function derived over a different time period during the first time period.

2. The method of claim 1, wherein the historical data further comprises physiological data associated with each epileptic event and the physiological data comprises an electroencephalography (EEG) signal received from a brain of the subject.

3. The method of claim 1, wherein the historical data further comprises physiological data associated with each epileptic event and the method further comprises:
generating a probabilistic model based on the physiological data associated with each epileptic event; and
weighting the probabilistic model based on the combined temporal probability model to generate a weighted probabilistic model of future seizure activity;
wherein the estimate of seizure probability is based on the combined temporal probability model.

4. The method of claim 1, wherein the probabilistic model is a logistic regression model.

5. The method of claim 4, wherein the historical data further comprises physiological data associated with each epileptic event and wherein generating the logistic regression model comprises:
determining, for a logistic regression classifier, a set of features in the physiological data; and
training the logistic regression model using the set of features.

6. The method of claim 5, wherein the set of features comprises:
a) a line length feature; and
b) one or more energy features, each of the one or more energy features being at a different frequency band.

7. The method of claim 5, further comprising applying a moving average filter to the set of features.

8. The method of claim 5, wherein the logistic regression model is trained to output the probability, P (S=1|X), that a feature vector, X, is pre-ictal.

9. The method of claim 5, wherein weighting the probabilistic model comprises:
updating the weights of the logistic regression classifier based on the temporal probability model.

10. The method of claim 1, wherein generating the temporal probability model comprises:
estimating each of the probability density function based on the times at which each epileptic event occurred over the different time periods during the first time period.

11. The method of claim 10, wherein the probability density function is estimated using kernel density estimation.

12. The method of claim 1, wherein the weighted probabilistic model is given by $$P(S=1\mid X) = \frac{1}{1+\exp\left(\log\frac{1-P_S}{P_S}+\log\frac{P(X\mid S=0)}{P(X\mid S=1)}\right)}$$

where $P_S$ represents the prior probability of a seizure occurring in one of the set of time windows.

13. The method of claim 1, wherein the historical data further comprises physiological data associated with each epileptic event and wherein the physiological data comprises one or more of:
heart rate data;
blood pressure data;
sweat data; and
movement data measured by an accelerometer worn by the patient.

14. The method of claim 1, wherein the time at which each epileptic event occurred is measured from the time of a previous epileptic event.

15. The method of claim 1, wherein the historical data further comprises values of one or more environmental variables associated with each epileptic event, and wherein the method further comprises:
generating an environmental probability model of future epileptic events based on the environmental variables associated with each epileptic event, the environmental probability model representing a probability of a future seizure occurrence over a range of values of the one or more environmental variable; and
weighting the probabilistic model based on the environmental probability model to generate the weighted probabilistic model of future seizure activity.

16. The method of claim 1, wherein the historical data further comprises values of one or more variables of sleep associated with each epileptic event, and wherein the method further comprises:
generating a sleep probability model of future epileptic events based on the sleep variables associated with each epileptic event, the sleep probability model representing a probability of a future seizure occurrence over a range of values of the one or more sleep variable; and
weighting the probabilistic model based on the sleep probability model to generate the weighted probabilistic model of future seizure activity.

17. The method of claim 1, further comprising:
outputting an estimate of seizure probability in the subject for one or more of the plurality of time windows using the combined temporal probability model.

18. A system, comprising:
an input for receiving historical data associated with epileptic events experienced by a subject over a first time period, the historical data comprising a time at which each epileptic event occurred;
a processor that
generates a combined temporal probability model of future epileptic events based on the time of each of the epileptic event, the combined temporal probability model representing a probability of a future seizure occurrence over a set of time windows, wherein the combined temporal probability model is generated by combining two or more probability density functions, each probability density function derived over a different time period during the first time period.

19. The system of claim 18, further comprising one or more measurement devices configured to record the physiological data.

20. The system of claim 18, wherein the one or measurement devices comprises an EEG sensor comprising a lead having at least one electrode for recording neural activity at a neural structure in a brain of the subject, wherein the physiological data comprises the recorded neural activity.

21. The system of claim 18, wherein the processor further:
outputs an estimate of seizure probability in the subject for one or more of the plurality of time windows using the combined temporal probability model.

\* \* \* \* \*